US012102659B2

(12) United States Patent
Szeto et al.

(10) Patent No.: US 12,102,659 B2
(45) Date of Patent: *Oct. 1, 2024

(54) METHODS FOR THE PREVENTION OR TREATMENT OF HEART FAILURE

(71) Applicants: Cornell University, Ithaca, NY (US); University of Washington, Seattle, WA (US)

(72) Inventors: Hazel H. Szeto, New York, NY (US); Peter S. Rabinovitch, Shoreline, WA (US); Dao-Fu Dai, Seattle, WA (US)

(73) Assignees: CORNELL UNIVERSITY, Ithaca, NY (US); UNIVERSITY OF WASHINGTON, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/079,604

(22) Filed: Dec. 12, 2022

(65) Prior Publication Data

US 2023/0285499 A1 Sep. 14, 2023

Related U.S. Application Data

(63) Continuation of application No. 16/796,940, filed on Feb. 20, 2020, now Pat. No. 11,534,476, which is a continuation of application No. 15/723,259, filed on Oct. 3, 2017, now abandoned, which is a continuation of application No. 14/727,513, filed on Jun. 1, 2015, now abandoned, which is a continuation of application No. 14/035,577, filed on Sep. 24, 2013, now abandoned, which is a continuation of application No. 12/897,325, filed on Oct. 4, 2010, now abandoned.

(60) Provisional application No. 61/289,483, filed on Dec. 23, 2009, provisional application No. 61/248,681, filed on Oct. 5, 2009.

(51) Int. Cl.
| A61K 38/07 | (2006.01) |
| A61K 9/00 | (2006.01) |
| A61K 45/06 | (2006.01) |
| A61P 9/00 | (2006.01) |
| C07K 5/09 | (2006.01) |
| C07K 5/107 | (2006.01) |
| C07K 5/11 | (2006.01) |

(52) U.S. Cl.
CPC ............ A61K 38/07 (2013.01); A61K 9/0019 (2013.01); A61K 45/06 (2013.01); A61P 9/00 (2018.01); C07K 5/0817 (2013.01); C07K 5/1016 (2013.01); C07K 5/1019 (2013.01)

(58) Field of Classification Search
CPC ...... A61K 38/07; A61K 9/0019; A61K 45/06; A61P 9/00; C07K 5/0817; C07K 5/1016; C07K 5/1019
See application file for complete search history.

(56) References Cited

U.S. PATENT DOCUMENTS

| 4,522,811 | A | 6/1985 | Eppstein et al. |
| 4,732,898 | A | 3/1988 | Badger et al. |
| 5,312,899 | A | 5/1994 | Schiller |
| 5,602,100 | A | 2/1997 | Brown et al. |
| 5,652,122 | A | 7/1997 | Frankel et al. |
| 5,674,534 | A | 10/1997 | Zale et al. |
| 5,716,644 | A | 2/1998 | Zale et al. |
| 5,885,958 | A | 3/1999 | Zadina et al. |
| 5,993,848 | A | 11/1999 | Suzuki et al. |
| 5,994,372 | A | 11/1999 | Yaksh |
| 6,221,355 | B1 | 4/2001 | Dowdy |
| 6,268,398 | B1 | 7/2001 | Ghosh et al. |
| 6,468,798 | B1 | 10/2002 | Debs et al. |
| 6,503,713 | B1 | 1/2003 | Rana |
| 6,703,483 | B1 | 3/2004 | Schiller |
| 6,759,520 | B1 | 7/2004 | Carr et al. |
| 6,859,662 | B2 | 2/2005 | Bombardini |
| 6,900,178 | B2 | 5/2005 | Oeltgen et al. |
| 7,498,297 | B2 | 3/2009 | Szeto et al. |
| 7,541,340 | B2 | 6/2009 | Szeto et al. |
| 7,550,439 | B2 | 6/2009 | Szeto |
| 7,576,061 | B2 | 8/2009 | Szeto et al. |
| 7,704,954 | B2 | 4/2010 | Szeto et al. |
| 7,718,620 | B2 | 5/2010 | Szeto et al. |
| 7,732,398 | B2 | 6/2010 | Szeto et al. |
| 7,781,405 | B2 | 8/2010 | Szeto |
| 7,811,987 | B2 | 10/2010 | Szeto et al. |
| 2003/0060415 | A1 | 3/2003 | Hung |
| 2004/0248808 | A1 | 12/2004 | Szeto et al. |

(Continued)

FOREIGN PATENT DOCUMENTS

| EP | 2 485 749 | 8/2012 |
| WO | WO-96/40073 A2 | 12/1996 |

(Continued)

OTHER PUBLICATIONS

Allison L Cirino, Hypertrophic Cardiomyopathy Overview. Aug. 5, 2008 [Updated Jul. 8, 2021]. In: Adam MP, Feldman J, Mirzaa GM, et al., editors. GeneReviews, pp. 1-16.*
Aitman, et al.; "Identification of CD36 (Fat) as an insulin resistance gene causing defective fatty acid and glucose metabolism in hypertensive rats"; Nature Genetics (Jan. 1999); vol. 21, pp. 76-83.
Alam, et al., "A Novel Peptide (MTP-131) that Improves Mitochondrial Function Reverses Visual Decline in Mouse Models of Metabolic Dysfunction Leading to Diabetes," American Diabetes Association, 2012, Poster Presentation, 1 page.
Alam, et al., "A novel Peptide that Improves Mitochondrial Function Reverses Diabetes- and Age-Related Visual Decline," American Aging Association, 2012, Abstract only, 1 page.
Alam, et al., "Reducing Mitochondrial Oxidative Stress to Treat Diabetes and Age-related Visual Decline," Society of Neuroscience, 2011, Poster Presentation, 1 page.

(Continued)

*Primary Examiner* — Jeanette M Lieb
*Assistant Examiner* — Erinne R Dabkowski
(74) *Attorney, Agent, or Firm* — Foley & Lardner LLP

(57) ABSTRACT

The disclosure provides methods of preventing or treating heart failure in a mammalian subject. The methods comprise administering to the subject an effective amount of an aromatic-cationic peptide to subjects in need thereof.

9 Claims, 9 Drawing Sheets

(56) References Cited

U.S. PATENT DOCUMENTS

| | | |
|---|---|---|
| 2004/0266675 A1 | 12/2004 | Anderson |
| 2005/0096333 A1 | 5/2005 | Dugar et al. |
| 2005/0148612 A1 | 7/2005 | Stamler et al. |
| 2005/0192215 A1 | 9/2005 | Ghosh et al. |
| 2007/0027087 A1 | 2/2007 | Szeto et al. |
| 2007/0093969 A1 | 4/2007 | Mendrick et al. |
| 2007/0129306 A1 | 6/2007 | Szeto et al. |
| 2007/0259377 A1 | 11/2007 | Urdea et al. |
| 2008/0014604 A1 | 1/2008 | Devarajan et al. |
| 2008/0027082 A1 | 1/2008 | Hocher et al. |
| 2009/0221514 A1 | 9/2009 | Szeto et al. |
| 2009/0253641 A1 | 10/2009 | Neufer et al. |
| 2011/0082084 A1 | 4/2011 | Szeto et al. |
| 2014/0100166 A1 | 4/2014 | Szeto et al. |
| 2016/0106800 A1 | 4/2016 | Szeto et al. |

FOREIGN PATENT DOCUMENTS

| | | |
|---|---|---|
| WO | WO-99/15154 A1 | 4/1999 |
| WO | WO-00/38651 A1 | 7/2000 |
| WO | WO-2004/070054 A3 | 4/2005 |
| WO | WO-2009/100363 A2 | 8/2009 |
| WO | WO-2009/108695 A2 | 9/2009 |
| WO | WO-2010/120431 A2 | 10/2010 |
| WO | WO-2011/019809 | 2/2011 |

OTHER PUBLICATIONS

Anderson, et al., "Mitochondrial H2O2 emission and cellular redox state link excess fat intake to insulin resistance in both rodents and humans," J. Clin. Invest., Mar. 2009, vol. 119, No. 3, pp. 573-581.

Anderson, et al., "Mitochondrial production of reactive oxygen species contributes to the ß- adrenergic stimulation of mouse cardiomycytes," J. Physiol., Mar. 30, 2011, vol. 589, Issue 7, pp. 1791-1801.

Brown, David A., "Mitochondrial Derived Cardioprotection in Exercised Hearts: Role of Cardiac Glutathione," American College of Sports Medicine, 2012, DB Lab Presentation, 28 pages.

Brown, et al., "Bendavia, a mitochondria-targeting peptide, reduces reperfusion injury and reactive oxygen species levels through a mechanism independent of direct oxygen radical scavenging: A multicenter study," American Heart Association, Nov. 20, 2012, vol. 126, Abstract only, 1 page.

Calkins, et al., "Impaired mitochondrial biogenesis, defective axonal transport of mitochondria, abnormal mitochondrial dynamics and synaptic degeneration in a mouse model of Alzheimer's disease," Hum. Mol. Genet., Dec. 1, 2011, vol. 20, No. 23, pp. 4515-4529.

CAO, et al., "Mitochondria-targeted antioxidant attenuates high glucose-induced P38 MAPK pathway activation in human neuroblastoma cells," Mol. Med. Report., Apr. 2012, vol. 5, Issue 4, pp. 929-934.

Cardoso, et al., "The Protective Effect of Vitamin E, Idebenone and Reduced Glutathione on Free Radical Mediated Injury in Rat Brain Synaptosomes," Biochemical and Biophysical Research Communications, 1998, vol. 246 No. 3, pp. 703-710.

Carter, et al., "Evaluation of the antioxidant peptide SS31 for treatment of burn-induced insulin resistance," Int. J. Mol. Med., Oct. 2011, vol. 28, Issue 4, pp. 589-594.

Chen, et al., "Mitochondria-targeted Peptide MTP-131 Alleviates Mitochondrial Dysfunction and Oxidative Damage in Human Trabecular Meshwork Cells," Invest. Ophthalmol. & Vis. Sci., Sep. 2011, vol. 52, No. 10, pp. 7027-7037.

Cheng, Longxian, "Progress in clinical application related with CGRP", Herald of Medicine, 1992, vol. 11, No. 3, 2 pages (no English translation provided).

Cho, et al., "A Novel Cell-permeable Antioxidant Peptide, SS31, Attenuates Ischemic Brain Injury by Down-regulating CD36,201D", J. Biol. Chem., Feb. 2007, vol. 282, No. 7, pp. 4634-4642.

Cho, et al., "Potent mitochondria-targeted peptides reduce myocardial infarction in rats," Coron. Artery Dis., May 2007, vol. 18, No. 3, pp. 215-220.

Chonn, et al., "Recent Advances in Liposomal Drug-Delivery Systems," Curr. Opin. Biotechnol., Dec. 1995, vol. 6, Issue 6, pp. 698-708.

Communication pursuant to Article 94(3) EPC on EP Patent Application No. 19175034.8 dated May 11, 2021 (3 pages).

Communication pursuant to Rule 69 EPC on EP Patent Application No. 19175034.8 dated Feb. 10, 2020 (2 pages).

Corpeleijn, et al., "Direct association of a promoter polymorphism in the CD36/FAT fatty acid transporter gene with Type 2 diabetes mellitus and insulin resistance," Diabetic Medicine, 2006, vol. 23, pp. 907-911.

Dai, et al., "Mitochondrial targeted antioxidant peptide ameliorates hypertensive cardiomyopathy," J. Am. Coll. Cardiol., Jun. 28, 2011, vol. 58, No. 1, pp. 73-82.

Drin, et al., "Studies on the Internalization Mechanism of Cationic Cell-penetrating Peptides," Journal of Biological Chemistry, 2003, vol. 27, No. 33, pp. 31192-31201.

Eirin, et al., "Mitochondrial Targeted Peptides Attenuate Myocardial Damage after Renal Revascularization in Experimental Atherosclerotic Renovascular Hypertension," American Society of Nephrology, Aug. 2012, Abstract and Figures, 2 pages.

Eirin, et al., "A Mitochondrial Permeability Transition Pore Inhibitor Improves Renal Outcomes After Revascularization in Experimental Atherosclerotic Renal Artery Stenosis," J. Am. Heart Assoc., Oct. 8, 2012, vol. 60, pp. 1242-1249; available at http://hyper.ahajournals.org/content/60/5/1242 and supplemental content available at http://hyper.ahajournals.org/content/suppl.2012/10/08/HYPERTENSIONAHA.112.199919.DC1.html (26 pages total).

Eirin, et al., "Chronic Treatment with Bendavia Preserves the Stenotic Kidney in Swine Atherosclerotic Renovascular Disease (ARVD)," American Society of Nephrology, 2012, Abstract and Figures, 2 pages.

Eirin, et al., "MTP-131 reduces renal injury after percutaneous transluminal renal angioplasty (PTRA) in swine atherosclerotic renal artery stenosis (ARAS)," American Society of Nephrology, 2011, Poster Presentation, 1 page.

English translation of Office Action in JP Patent Application No. 2015-050464 dated Feb. 10, 2016 (2 pages).

English Translation of First Office Action in CN Patent Application No. 201410049107.5 dated Jan. 13, 2015 (8 pages).

English Translation of Office Action issued in JP Patent Application No. 2012-532388 dated Sep. 16, 2014 (2 pages).

Extended European Search Report in EP Patent Application 16169795.8 dated Nov. 2, 2016.

Extended European Search Report in EP Patent Application No. 14151500.7 dated Jul. 16, 2014 (9 pages).

Extended European Search Report in EP Patent Application No. 15154763.5 dated Aug. 19, 2015 (11 pages).

Extended European Search Report on EP Patent Application No. 19175034.8 dated Nov. 15, 2019 (12 pages).

Febbraio, et al., "CD36: Implications in Cardiovascular Disease," Int J Biochem Cell Biol, 2007, vol. 39, No. 11, pp. 2012-2030.

Final Office Action in U.S. Appl. No. 15/723,259 dated Oct. 1, 2019.

Final Office Action in U.S. Appl. No. 16/796,940 dated Dec. 23, 2020 (22 pages).

First Office Action and Examination Report received in Canadian Patent Application No. 2776581 dated May 30, 2016, 3 pages.

Fuhrman, et al., "Oxidative stress increases the expression of the CD36 scavenger receptor and the cellular uptake of oxidized low-density lipoprotein in macrophages from atherosclerotic mice: protective role of antioxidants and of paraoxonase," Atherosclerosis, Apr. 2002, vol. 161, pp. 307-316.

Gilliam, et al., "Doxorubicin acts via mitochondrial ROS to stimulate catabolismin C2C12 myotubes," Am. J. Physiol. Cell Physiol., Sep. 2011, vol. 302, Issue 1, pp. C195-C202.

Giorgio, et al., "The effects of idebenone on mitochondrial bioenergetics," Biochimica et Biophysica Acta, Feb. 2012, vol. 1817, No. 2, pp. 363-369.

(56) References Cited

OTHER PUBLICATIONS

Gregoriardis, "Engineering Liposomes for Drug Delivery: Progress and Problems," TIBTECH, Dec. 1995, vol. 13, pp. 527-537, 11 pages.
Gustafsson, et al., "Heart mitochondria: gates of life and death", Cardiovascular Research, 2008, vol. 77, pp. 334-343.
Gutkowska, et al., "The Cardiovascular and Renal Effects of the Potent and Highly Selective mu Opioid Agonist [Dmt1] DALDA," J Cardiovascular Pharmacology, 2004, vol. 44, pp. 651-658.
Hale, et al., "A Novel Mitochondrial Permeability Transition Pore Inhibitor, Bendavia, Reduces, Microvascular Obstruction (No-Reflow) due to Myocardial Ischemia/Reperfusion Injury in the Rabbit," Basic Cardiovascular Sciences, 2011, Poster Presentation, 1 page.
Han, et al., "Mitochondria-Derived Reactive Oxygen Species Mediate Heme Oxygenase-1 Expression in Sheared Endothelial Cells"; J. Pharmacol. Exp. Ther., 2009, vol. 329, No. 1, pp. 94-101.
Hausse, et al. "Idebenone and reduced cardiac hypertrophy in Friedreich's ataxia" Cardiovascular Medicine, 2002, vol. 87, pp. 346-349.
Hill, et al., "Antioxidant and Oxidative Stress Changes during Heart Failure Subsequent to Myocardial Infarction in Rats," American Journal of Pathology, Jan. 1996, vol. 148, No. 1, pp. 291-300.
International Preliminary Report on Patentability in International Patent Application No. PCT/US2010/051329 mailed Apr. 19, 2012 (6 pages).
International Search Report and Written Opinion in International Patent Application No. PCT/US2010/51329 dated Nov. 19, 2010.
Javadov, et al., "Mitochondrial Permeability Transition Pore Opening as a Promising Therapeutic Target in Cardiac Diseases", The Journal of Pharmacology and Experimental Therapeutics, 2009, vol. 330, No. 3, pp. 670-678.
Kai et al, "Pressure Overload-Induced Transient Oxidative Stress Mediates Perivascular Inflammatin and Cardiac Fibrosis through Angiotensin II," Hypertension Res., 2006, vol. 29, pp. 711-718.
Kett, et al., "Baroreflex-Mediated Bradycardia but Not Tachycardia is Blunted Peripherally by Intravenous μ-opioid Agonists," American Journal of Obstetrics and Gynecology, May 1998, vol. 178, No. 5, pp. 950-955.
Kloner, et al., "Reduction of Ischemia/Reperfusion Injury with Bendavia, a Mitochondria-Targeting Cytoprotective Peptide," J. Am. Heart Assoc., 2012, vol. 1, 14 pages, available at http://jaha.ahajournals.org/content/1/3/e001644.
Kloner, et al., "Bendavia, a Novel Mitochondrial-Targeted Cytoprotective Compound Reduces Ischemia/Reperfusion Injury: Experience in 3 Independent Laboratories," American Heart Association, 2011, Abstract only, 2 pages.
Lee, et al., "Novel Mitochondria-Targeted Antioxidant Peptide Ameliorates Burn-Induced Apoptosis and Endoplasmic Reticulum Stress in the Skeletal Muscle of Mice," Shock, 2011, vol. 36, No. 6, pp. 580-585.
Li, et al., Mitochondria-targeted antioxidant peptide SS31 attenuates high glucose-induced injury on human retinal endothelial cells, Biochem. & Biophys. Res. Commun., 2011, vol. 404, pp. 349-356.
Liang, et al., "SS31 protects human RPE cells from oxidative damage and reduces laser-induced choroidal neovascularization," Association for Research in Vision and Opthamology, 2010, Poster Presentation, 1 page.
Lichtenberg, et al., "Liposomes: Preparation, Characterization and Preservation," Methods of Biochemical Analysis, Mar. 16, 1988, vol. 33, pp. 337-462.
Lishmanov et al., "Ligands for opioid and o-receptors improve cardiac electrical stability in rat models of post-infarction cardiosclerosis and stress," Life Sciences, 65:13-17, 1999.
Liu, et al., "Mitochondria-targeting peptide (SS-31) promotes rapid repair of actin cytoskeleton following ischemia and protects tubular epithelial cell architecture," American Society of Nephrology, 2012, vol. 2, Abstract only, 1 page.
Liu, Shaoyi et. al., "Boosting mitochondrial function to minimize ischemia-reperfusion injury," Experimental Biology, (2011), Poster Presentation (1 page).
Ma, et al., "Superoxide Flashes: Early Mitochondrial Signals for Oxidative Stress-Induced Apoptosis," J. Biol. Chem., Aug. 2011, vol. 286, No. 31, pp. 27573-27581.
Manczak, et al., "Mitochondria-Targeted Antioxidants Protect Against Amyloid-ß toxicity in Alzheimer's Disease Neurons," J. Alzheimer's Dis., 2010, vol. 20, pp. S609-S631.
Marcinek, et al., "Acute pharmacological intervention reverses mitochondrial deficits and improves function in aged skeletal muscle," American Aging Association, 2012, Abstract only, 1 page.
Min, et al., "Mitochondrial-targeted antioxidants attenuate immobilization-induced skeletal muscle atrophy," Experimental Biology Meeting 2010, Anaheim CA, USA, Apr. 24-28, 2010, FASEB Journal, 2010, vol. 24, Abstract lb670, 1 page.
Min, et al., "Mitochondrial-targeted antioxidants protect skeletal muscle against immobilization-induced muscle atrophy," J. Appl. Physiol., 2011, vol. 111, No. 5, pp. 1459-1466.
Mizuguchi, et al., "A novel cell-permeable antioxidant peptide decreases renal tubular apoptosis and damage in unilateral ureteral obstruction," Am. J. Physiol. Renal Physiol., 2008, vol. 295, pages F1545-1553.
Mizuguchi, et al., "Intratumor administration of fusogenic liposomes containing fragment A of diphtheria toxin suppresses tumor growth." Cancer Lett., Feb. 26, 1996, vol. 100, Issue 1, pp. 63-69.
Molecular Cardiovascular Medicine, 2007, vol. 8, No. 2, p. 105-112.
Moosmann, et al., "Secretory Peptide Hormones Are Biochemical Antioxidants: Structure-Activity Relationship," Mol. Pharmacol., 2002, vol. 61, No. 2, pp. 260-268.
Nieborowska-Skorska, et al., "Rac2-MRC-clII-generated ROS cause genomic instability in chronic myeloid leukemia stem cells and primitive progenitors," Blood, 2012, vol. 119, No. 18, pp. 4253-4263.
Non-Final Office Action in U.S. Appl. No. 12/897,325 dated Mar. 26, 2013 (15 pages).
Non-Final Office Action in U.S. Appl. No. 14/035,577 dated Dec. 3, 2014, 28 pages.
Non-Final Office Action in U.S. Appl. No. 14/727,513 dated Aug. 24, 2016.
Non-Final Office Action in U.S. Appl. No. 15/723,259 dated Jan. 18, 2019.
Non-Final Office Action in U.S. Appl. No. 16/796,940 dated Aug. 3, 2020.
Notice of Allowance on U.S. Appl. No. 16/796,940 Dtd Aug. 25, 2022.
Office Action in CA Patent Application No. 2,776,581 mailed Jun. 30, 2017.
Office Action in JP Patent Application No. 2016-156631 mailed Mar. 5, 2018.
Office Action on CA Patent Application No. 2776581 dated Jun. 14, 2019 (3 pages).
Office Action on JP Patent Application No. 2018-165223 dated Aug. 26, 2019 (6 pages) (with English Translation).
Office Action on JP Patent Application No. JP 2020-030241 dated Apr. 15, 2021 (with English translation) (4 pages).
Official Action in CA Patent Application No. 2776581 mailed Jun. 14, 2018.
Omoniyi, et al., "A peripheral site of action for the attenuation of baroreflex-mediated bradycardia by intravenous u-opioid agonists," Journal of Cardiovascular Pharmocolgy, 2000, vol. 35, No. 2, pp. 269-274.
Petri, et al., "Cell-permeable peptide antioxidants as a novel therapeutic approach in a mouse model of amyotrophic lateral sclerosis," Journal of Neurochemistry, 2006, vol. 98, pp. 1141-1148.
Powers, et al., "Mitochondria-targeted antioxidants protect against mechanical-ventilation-induced diaphragm weakness," Crit. Care Med., 2011, vol. 39, No. 7, pp. 1749-1759.
Putney, "Encapsulation of proteins for improved delivery," Current Opinion in Chemical Biology, Aug. 1998, vol. 2, No. 4, pp. 548-552.

(56) References Cited

OTHER PUBLICATIONS

Rabinovitch, Peter, "Mitochondrial Oxidative Stress and Cardiac Aging," Basic Cardiovascular Sciences, 2011, Presentation, 19 pages.
Reddy, "Controlled-Release, Pegylation, Liposomal Formulations: New Mechanisms in the Delivery of Injectable Drugs," Ann Pharmacother., Jul./Aug. 2000, vol. 34, pp. 915-923.
Reddy, et al., "Toxicity of Neurons Treated with Herbicides and Neuroprotection by Mitochondria- Targeted Antioxidant SS31," Int. J. Environ. Res. & Public Health, 2011, vol. 8, pp. 203-221.
Reddy, P. Hemachandra, "Amyloid beta Toxicity, Mitochondrial Dysfunction and Synaptic Damage in Alzheimer's Disease: Implications for Mitochondria-Targeted Antioxidant Therapeutics," New York Academy of Sciences, 2010, Abstract only, 1 page.
Restriction Requirement on U.S. Appl. No. 16/796,940, dated May 4, 2020, 5 pages.
Ricci, et al., "Involvement of the mitochondrial permeability transition pore in angiotensin II-mediated apoptosis," Exp. Clin Cardio, 2005, vol. 10, No. 3, pp. 160-164.
Richard, et al., "Cell-penetrating Peptides," Journal of Biological Chemistry, 2003, vol. 278, No. 1, pp. 585-590.
Rustin, et al. "Effect of idebenone on cardiomyopathy in Friedreich's ataxia: a preliminary study," The Lancet, 1999, vol. 354, pp. 477-479.
Sabbah, et al., "Acute Intravenous Infusion of Bendavia (MTP-131), A Novel Mitochondria-Targeting Peptide, Improves Left Ventricular Systolic Function in Dogs With Advanced Heart Failure," American Heart Association, Nov. 20, 2012, Abstract, 1 page.
Saito, et al., "Iron chelation and a free radical scavenger suppress angiotensin II-induced upregulation of TGB-beta1 in the heart," Am J Physiol Heart Circ Physiol, 2005, vol. 288, pp. H1836-H1843.
Schiller, et al., "Dermorphin analogues carrying an increased positive net charge in their "message" domain display extremely high μ-opioid receptor selectivity," J. Med. Chem., 1989, vol. 32, No. 3, pp. 698-703.
Schiller, et al., "Synthesis and In Vitro Opioid Activity Profiles of DALDA Analogues," European Journal of Medicinal Chemistry, Oct. 2000, vol. 35, Issue 10, pp. 895-901.
Search Report and First Office Action in CN Patent Application No. 201080055190.7 dated Aug. 1, 2013 (English translation only) (7 pages).
Sharma, et al., "Mitochondrial respiratory complex I dysfunction promotes tumorigenesis through ROS alteration and AKT activation," Hum. Mol. Genet., 2011, vol. 20, No. 23, pp. 4605-4616.
Shimada et al., "Effects of Losartan on Left Ventricular Hypertrophy and Fibrosis in Patients with Nonobstructive Hypertrophic Cardiomyopathy," JAAC Heart Fail. Dec. 2013, pp. 480-487.
Shimoyama, et al., "Antinociceptive and respiratory effects of intrathecal H-Tyr-D-Arg-Phe-Lys-NH2 (DALDA) and [Dmtl] DALDA," The Journal of Pharmacology and Experimental Therapeutics, 297(1):364-371, 2001.
Shroff, et al., "Effects of intrathecal opioid on extubation time, analgesia and intensive care unit stay following coronary artery bypass grafting," Journal of Clinical Anesthesia, 1997, vol. 9, pp. 415-419.
Sloan, et al., "Mitochondrial permeability transition in the diabetic heart: Contributions of thiol redox state and mitochondrial calcium to augmented reperfusion injury," J. Mol. Cell. Cardiol., 2012, vol. 52, pp. 1009-1018.
Song, et al., "A Potent Opiate Agonist Protects Against Myocardial Stunning During Myocardial Ischemia and Reperfusion in Rats," Coronary Artery Disease, 2005, vol. 16, No. 6, pp. 407-410.
Stanley, et al., "Myocardial Structure Metabolism in the Normal and Failing Heart," Physiol Rev, 2005, vol. 85, pp. 1093-1129.
Szeto et al., "Mitochondria-Targeted Peptide Accelerates ATP Recovery and Reduces Ischemic Kidney Injury," J Am Soc Nephrol, 2011, vol. 22, pp. 1041-1052.
Szeto, et al., "In Vivo Disposition of Dermorphin Analog (DALDA) in Nonpregnant and Pregnant Sheep1," The Journal of Pharmacology and Experimental Therapeutics, 1998, vol. 284, No. 1, pp. 61-65.
Szeto, et al., "In vivo Pharmacokinetics of Selective μ-Opioid Peptide Agonists," The Journal of Pharmacology and Experimental Therapeutics, 2001, vol. 298, No. 1, pp. 57-61.
Szeto, et al., "Novel Therapies Targeting Inner Mitochondrial Membrane—from Discovery to Clinical Development", Pharm. Res., 2011, vol. 28, pp. 2669-2679.
Szeto, et al., "Respiratory depression after intravenous administration of d-selective opioid peptide analogs," Peptides, 1999, vol. 20, pp. 101-105.
Szeto, et al., "Mitochondria-targeting peptide (SS-31, Bendavia®) prevents microvascular rarafaction, inflammation, and fibrosis caused by ischemia-reperfusion injury," American Society of Nephrology, 2012, Abstract only, 1 page.
Szeto, et al., "Rapid Restoration of ATP by SS-31, an Inhibitor of Mitochondrial Permeability Transition, Prevents Tubular Cytoskeletal Rearrangement in Renal Ischemia-Reperfusion Injury," American Society of Nephrology, 2010, Poster Presentation, 1 page.
Szeto, H. "Development of Mitochondria-targeted Aromatic-cationic Peptides for Neurodegenerative Diseases," Ann. N.Y. Acad. Sci., 2008, vol. 1147, pp. 112-121.
Szeto, Hazel H., "Cell-permeable, Mitochondrial-targeted, Peptide Antioxidants," The AAPS Journal, 2006, vol. 8, No. 2, Article 32, pages E277-E283.
Szeto, Hazel H., "Mitochondria-Targeted Cytoprotective Peptides for Ischemia-Reperfusion Injury," Antioxidants & Redox Signaling, Nov. 2008, vol. 10, No., 3, pp. 601-619.
Szeto, Hazel H., "Mitochondrial Protection as Strategy to treat Ischemia-Reperfusion Injury," American Society of Nephrology, 2010, Presentation, 17 pages.
Szeto, Hazel H., "The development of a therapeutic peptide for mitochondrial protection—from bench to bedside," Experimental Biology, 2011, Poster Presentation, 1 page.
Szeto, Hazel, "Mitochondria-Targeted Peptide Antioxidants: Novel Neuroprotective Agents," The AAPS Journal, 2006, vol. 8, No. 3, Article 62, pp. E521-E531.
Thomas, et al., "Mitochondrial Targeting with Antioxidant Peptide SS-31 Prevents Mitochondrial Depolarization, Reduces Islet Cell Apoptosis, Increases Islet Cell Yield, and Improves Posttransplantation Function", J. Am. Soc. Nephrol., 2007 Vol. 18 pp. 213-222.
Tiganis, Tony, "Reactive Oxygen Species & NAPDH Oxidases in Insulin Signalling," NOX Gordon Research Conference, Jun. 3-8, 2012, Presentation, 44 pages.
Tojo, et al., "Angiotensin II and Oxidative Stress in Dahl Salt-Sensitive Rat with Heart Failure," Hypertension, 2002, vol. 40, pp. 834-839.
Unger, et al., "Hyperglycemia as an inducer as well as a consequence of impaired islet cell function and insulin resistance: implications for the management of diabetes," Diabetologia, 1985, vol. 28, No. 3, pp. 119-121.
Wang, Dantong et al., "Elevated Mitochondrial Reactive Oxygen Species Generation Affects the Immune Response via Hypoxia-Inducible Factor-1a in Long-Lived Mclk1+/- Mouse Mutants," J. Immunol., 2010, vol. 184, No. 2, pp. 582-590.
Weiner, Alan L., "Liposomes for Protein Delivery: Selecting Manufacture and Development Processes," Immunomethods, Jun. 1994, vol. 4, No. 3, pp. 201-209.
Wells, "Additivity of Mutational Effects in Proteins," Biochemistry, American Chemical Society, 1990, vol. 29, No. 37, pp. 8509-8517.
Whiteman, Matthew et al., "Do Mitochondriotropic Antioxidants Prevent Chlorinative Stress-Induced Mitochondrial and Cellular Injury?" Antioxid. Redox Signal., 2008, vol. 10, No. 3, pp. 641-650.
Wu, et al., "A highly potent peptide analgesic that protects against ischemia-reperfusion-induced myocardial stunning," Am. J. Physioll Heart Circ. Physiol., 2002, vol. 283, pp. H783-H791.
Yang, et al., "Mitochondria Targeted Peptides Protect against 1-Methyl-4-Phenyl-1,2,3,6-Tetrahydropyridine Neurotoxicity," Antioxid Redox Signal., 2009, vol. 11, No. 9, pp. 2095-2104.

(56) References Cited

OTHER PUBLICATIONS

Yang, et al., "Socium tanshinone IIA Sulfonate attenuates angiotensin II-induced collagen type I expression in cardiac fibroblasts in vitro," Experimental and Molecular Medicine, Jul. 2009, vol. 41, No. 7, pp. 508-516.

Yoshihara, et al., "Antioxidants: Benefits and risks for long-term health," Maturitas, 2010, vol. 67, pp. 103-107.

Zhang, et al., "Role of mitochondria in angiotensin II-induced reactive oxygen species and mitogen-activated protein kinase activation," Cardiovascular Research, 2007, vol. 76, No. 2, pp. 204-212.

Zhao, et al., "Cell-permeable Peptide Antioxidants Targeted to Inner Mitochondrial Membrane inhibit Mitochondrial Swelling, Oxidative Cell Death, and Reperfusion Injury," J. Biol. Chem., Aug. 2004, vol. 279, No. 33, pp. 34682-34690.

Zhao, et al., "Oxidative stress mediates cardiac fibrosis by enhancing transforming growth factor-beta1 in hypertensive rates," Molecular and Cellular Biochemistry, Oct. 2008, vol. 317, Issue 1, pp. 43-50.

Zhao, et al., "Transcellular Transport of a Highly Polar 3+ Net Charge Opioid Tetrapeptide," Journal of Pharmacology and Experimental Therapeutics, 2003, vol. 304, No. 1, pp. 425-432.

Zhao, et al., "Mitochondria-targeted peptide prevents mitochondrial depolarization and apoptosis induced by tert-butyl hydroperoxide in neuronal cell lines," Biochem. Pharmacol., 2005, vol. 70, pp. 1796-1806.

Zhu, et al., "Histone Deacetylase-3 Activation Promotes Tumor Necrosis Factor-a (TNF-a) Expression in Cardiomyocytes during Lipopolysaccharide Stimulation," J. Biol. Chem., Mar. 2010, vol. 285, No. 13, pp. 9429-9436.

Zhu, et al., "MicroRNA-195 promotes palmitate-induced apoptosis in cardiomyocytes by down-regulating Sirtl," Cardiovasc. Res., Oct. 1, 2011, vol. 92, No. 1, pp. 75-84.

Communication pursuant to Article 94(3) EPC on EP Patent Application No. 19175034.8 dated Nov. 28, 2023 (5 pages).

\* cited by examiner

METHODS FOR THE PREVENTION OR TREATMENT OF HEART FAILURE

CROSS-REFERENCE TO RELATED APPLICATIONS

This application is a continuation of U.S. patent application Ser. No. 16/796,940, filed Feb. 20, 2020, now U.S. Pat. No. 11,534,476, which is a continuation of U.S. patent application Ser. No. 15/723,259, filed Oct. 3, 2017, now abandoned, which is a continuation of U.S. patent application Ser. No. 14/727,513, filed Jun. 1, 2015, now abandoned, which is a continuation of U.S. patent application Ser. No. 14/035,577, filed Sep. 24, 2013, now abandoned, which is a continuation of U.S. patent application Ser. No. 12/897,325, filed Oct. 4, 2010, now abandoned, which claims priority from U.S. Provisional Patent Application No. 61/248,681, filed Oct. 5, 2009, and U.S. Provisional Patent Application No. 61/289,483, filed Dec. 23, 2009, the entire contents of these applications are hereby incorporated by reference in their entireties.

GOVERNMENT SUPPORT

This invention was made with United States government support awarded by the following agency: NIH R01 HL101186, P30 AG013280, and P01 AG001751. The United States government has certain rights in this invention.

TECHNICAL FIELD

The present technology relates generally to compositions and methods of preventing or treating heart failure. In particular, the present technology relates to administering aromatic-cationic peptides in effective amounts to prevent or treat heart failure in mammalian subjects.

BACKGROUND

The following description is provided to assist the understanding of the reader. None of the information provided or references cited is admitted to be prior art to the present invention.

Heart failure is a leading cause of mortality and morbidity worldwide. In the United States, it affects nearly 5 million people and is the only major cardiovascular disorder on the rise. It is estimated that 400,000 to 700,000 new cases of heart failure are diagnosed each year in the U.S. and the number of deaths in the U.S. attributable to this condition has more than doubled since 1979, currently averaging 250,000 annually. Although heart failure affects people of all ages, the risk of heart failure increases with age and is most common among older people. Accordingly, the number of people living with heart failure is expected to increase significantly as the elderly population grows over the next few decades. The causes of heart failure have been linked to various disorders including coronary artery disease, past myocardial infarction, hypertension, abnormal heart valves, cardiomyopathy or myocarditis, congenital heart disease, severe lung disease, diabetes, severe anemia, hyperthyroidism, arrhythmia or dysrhythmia.

Heart failure (HF), also called congestive heart failure, is commonly characterized by decreased cardiac output, decreased cardiac contractility, abnormal diastolic compliance, reduced stroke volume, and pulmonary congestion. The clinical manifestations of heart failure reflect a decrease in the myocardial contractile state and a reduction in cardiac output. Apart from deficiencies in cardiac contractility, the HF disease state may arise from left ventricular failure, right ventricular failure, biventricular failure, systolic dysfunction, diastolic dysfunction, and pulmonary effects. A progressive decrease in the contractile function of cardiac muscle, associated with heart disease, often leads to hypoperfusion of critical organs.

SUMMARY

The present technology relates generally to the treatment or prevention of heart failure in mammals through administration of therapeutically effective amounts of aromatic-cationic peptides to subjects in need thereof. In particular embodiments, the aromatic-cationic peptides treat or prevent heart failure by enhancing mitochondrial function in cardiac tissues.

In one aspect, the disclosure provides a method of treating or preventing heart failure or hypertensive cardiomyopathy, comprising administering to said mammalian subject a therapeutically effective amount of an aromatic-cationic peptide. In some embodiments, the aromatic-cationic peptide is a peptide having:

at least one net positive charge;

a minimum of four amino acids;

a maximum of about twenty amino acids;

a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1. In particular embodiments, the mammalian subject is a human.

In one embodiment, $2p_m$ is the largest number that is less than or equal to r+1, and a may be equal to $p_t$. The aromatic-cationic peptide may be a water-soluble peptide having a minimum of two or a minimum of three positive charges.

In one embodiment, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In one embodiment, the peptide comprises a tyrosine or a 2',6'-dimethyltyrosine (Dmt) residue at the N-terminus. For example, the peptide may have the formula Tyr-D-Arg-Phe-Lys-NH$_2$ (SS-01) or 2',6'-Dmt-D-Arg-Phe-Lys-NH$_2$ (SS-02). In another embodiment, the peptide comprises a phenylalanine or a 2',6'-dimethylphenylalanine residue at the N-terminus. For example, the peptide may have the formula Phe-D-Arg-Phe-Lys-NH$_2$ (SS-20) or 2',6'-Dmp-D-Arg-Phe-Lys-NH$_2$. In a particular embodiment, the aromatic-cationic peptide has the formula D-Arg-2',6'-Dmt-Lys-Phe-NH$_2$ (referred to interchangeably as SS-31, MTP-131, or Bendavia™).

In one embodiment, the peptide is defined by formula I:

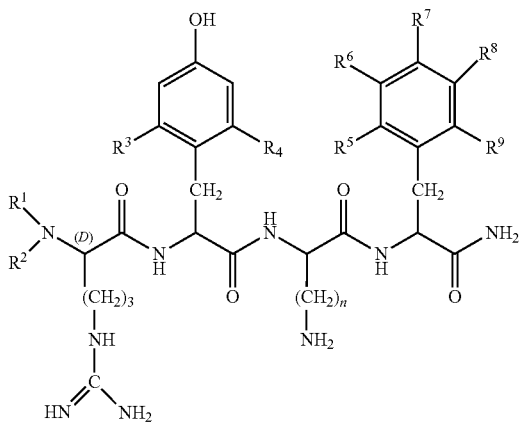

wherein $R^1$ and $R^2$ are each independently selected from
(i) hydrogen;
(ii) linear or branched $C_1$-$C_6$ alkyl;

(iii)

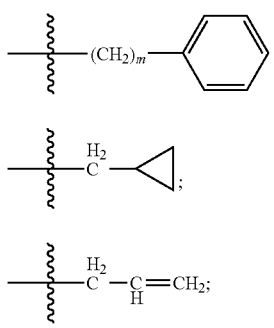

where m = 1-3;

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;
$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.
In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the peptide is defined by formula II:

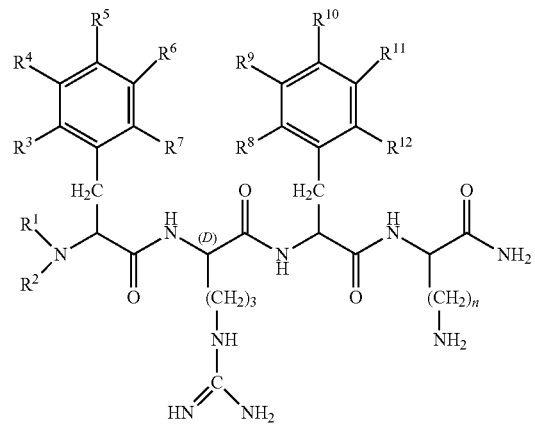

wherein $R^1$ and $R^2$ are each independently selected from
(i) hydrogen;
(ii) linear or branched $C_1$-$C_6$ alkyl;

(iii)

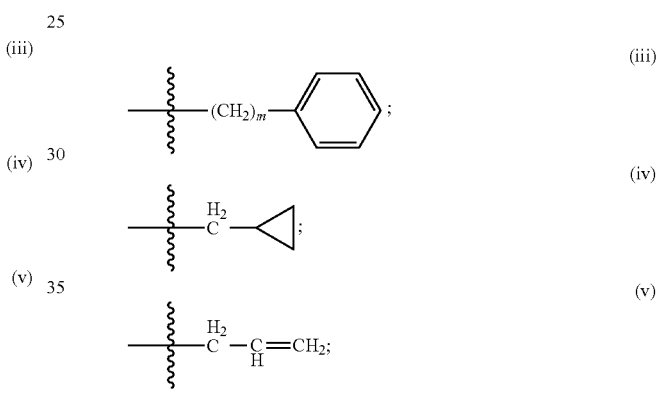

where m = 1-3

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.
In a particular embodiment, $R^1$, $R^2$, $R^3$, $R^4$, $R^5$, $R^6$, $R^7$, $R^8$, $R^9$, $R^{10}$, $R^1$, and $R^{12}$ are all hydrogen; and n is 4. In another embodiment, $R^1$, $R^2$, $R^3$, $R^4$, $R^5$, $R^6$, $R^7$, $R^9$, and $R^{11}$ are all hydrogen; $R^8$ and $R^{12}$ are methyl; $R^{10}$ is hydroxyl; and n is 4.

In one embodiment, the subject is suffering from heart failure. In one embodiment, the heart failure results from hypertension; ischemic heart disease; exposure to a cardiotoxic compound; myocarditis; thyroid disease; viral infection; gingivitis; drug abuse; alcohol abuse; pericarditis; atherosclerosis; vascular disease; hypertrophic cardiomyopathy; acute myocardial infarction; left ventricular systolic dysfunction; coronary bypass surgery; starvation; an eating disorder; or a genetic defect. In one embodiment, the subject is suffering hypertensive cardiomyopathy.

In one embodiment, myocardial contractility and cardiac output in the subject administered the peptide are increased compared to a control subject not administered the peptide. In one embodiment, the myocardial contractility and cardiac output in the subject are increased at least 10% compared to a control subject not administered the peptide.

In one embodiment, the method further comprises separately, sequentially or simultaneously administering a cardiovascular agent to the subject. In one embodiment, the cardiovascular agent is selected from the group consisting of: an anti-arrhythmia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, a digitalis formulation, an inotrope, and an antihyperlipidemic drug.

In another aspect, the disclosure provides a method for increasing myocardial contractility and cardiac output in a subject suffering from heart failure or hypertensive cardiomyopathy comprising administering to the subject a therapeutically effective amount of the peptide D-Arg-2'6'-Dmt-Lys-Phe-NH$_2$ or Phe-D-Arg-Phe-Lys-NH$_2$.

The aromatic-cationic peptides may be administered in a variety of ways. In some embodiments, the peptides may be administered orally, topically, intranasally, intraperitoneally, intravenously, subcutaneously, or transdermally (e.g., by iontophoresis).

BRIEF DESCRIPTION OF THE FIGURES

FIG. 2A: Representative blood pressure tracings of mice at baseline and after Ang II (1.1 mg/kg/d) administered with a subcutaneous pump. FIG. 2B: Ang II significantly increased systolic blood pressure by 27.2 mm Hg and diastolic pressure by 24.8 mm Hg.

FIG. 3A: Ang 11 (1.1 mg/kg/d) for 4 weeks substantially increased LVMI in WT control mice. Simultaneous administration of SS-31 (3 mg/kg/d) significantly attenuated the Ang II-induced increase in LVMI (left panel), to a similar extent as that observed in mice with inducible overexpression of mitochondrial catalase (i-mCAT, right panel). FIG. 3B and FIG. 3C: Left ventricular end-diastolic diameter (LVEDD) and fractional shortening (FS,%) were not significantly changed after 4 weeks of Ang II in the presence or absence of mitochondrial antioxidants. FIG. 3D: Diastolic function measured by tissue Doppler imaging of Ea/Aa significantly reduced after 4 weeks of Ang II, but this is significantly ameliorated by SS-31 or genetic overexpression of mCAT.

FIG. 4A: Ang II significantly increased heart weight (normalized to tibia length) and this was significantly attenuated by SS-31. FIG. 4B: Quantitative PCR showed a dramatic increase in atrial natriuretic peptide (ANP) gene expression, which was significantly prevented by SS-31. FIG. 4C: Representative histopathology shows substantial perivascular fibrosis (PVF) and interstitial fibrosis (IF) after Ang II, which was better protected in SS-31 treated hearts. FIG. 4D: Quantitative analysis of blue trichrome staining demonstrated a significant increase in ventricular fibrosis after Ang II, and this was substantially attenuated by SS-31. FIG. 4E: Quantitative PCR showed upregulation of pro-collagen1a2 mRNA after Ang II, which was significantly reduced in SS-31 hearts.

FIG. 5A: Ang 11 for 4 weeks significantly increased cardiac mitochondrial protein carbonyl content, an indicator of protein oxidative damage, and this was significantly ameliorated by SS-31. FIG. 5B: Quantitative PCR revealed significant upregulation of genes in mitochondrial biogenesis, all of which were attenuated by SS-31. *p<0.05 compared with saline group, #p<0.05 compared with Ang II treated group.

FIG. 6A: NADPH oxidase activity was significantly increased after Ang II. No significant effect of SS-31 was observed. FIG. 6B: Ang II for 4 weeks substantially induced apoptosis, as shown by increase in cleaved (activated) caspase 3 and this was significantly attenuated by SS-31. FIG. 6C: Phosphorylation of p38 MAP kinase significantly increased after Ang II, which was substantially lower in SS-31 treated hearts (upper panel). Protein levels of p38 MAP kinase also increased after Ang II.

FIG. 7A: SS-31 (3 mg/kg/d) for 4 weeks (from age 12 to 16 weeks) significantly ameliorated the decline in systolic function, as indicated by FS, in Gαq overexpressing mice. FIG. 7B and FIG. 7C: Chamber enlargement and impairment of diastolic function in Gαq mice were slightly attenuated by SS-31 with borderline significance, p=0.08 and 0.06, respectively. FIG. 7D: Worsening of myocardial performance index (MPI) in Gαq mice was significantly ameliorated by SS-31. FIG. 7E: An increase in normalized heart weight in Gαq mice was substantially protected by SS-31, while increased normalized lung weight displayed a modest effect from SS-31 with borderline significance (p=0.09).

FIG. 9C shows cardiac mitochondrial protein carbonyl content significantly increased after Ang 11, which was reduced by SS-31.

DETAILED DESCRIPTION

Figure 1:
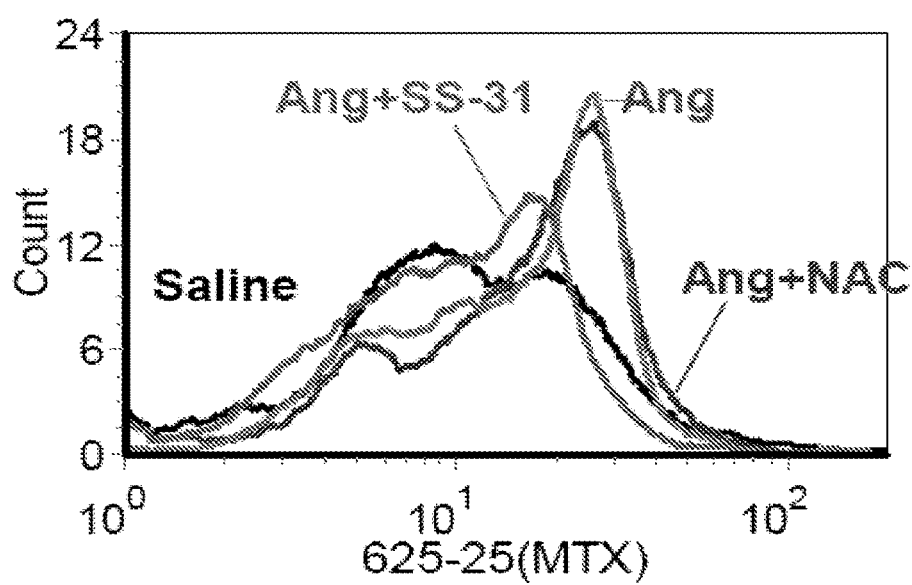
FIG. 1 is a graph of flow cytometric analysis of neonatal cardiomyocytes stimulated with Ang II (1 μM) and loaded with Mitosox (5 μM), an indicator of mitochondrial ROS.

It is to be appreciated that certain aspects, modes, embodiments, variations and features of the invention are described below in various levels of detail in order to provide a substantial understanding of the present invention. The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in the prevention of, or a decrease in, heart failure or one or more symptoms associated with heart failure. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds. In the methods described herein, the aromatic-cationic peptides may be administered to a subject having one or more signs or symptoms of heart failure, such as cardiomegaly, tachypnea, and hepatomegaly. For example, a "therapeutically effective amount" of the aromatic-cationic peptides is meant levels in which the physiological effects of a heart failure are, at a minimum, ameliorated.

As used herein, the terms "congestive heart failure" (CHF), "chronic heart failure", "acute heart failure", and "heart failure" are used interchangeably, and refer to any condition characterized by abnormally low cardiac output in which the heart is unable to pump blood at an adequate rate or in adequate volume. When the heart is unable to adequately pump blood to the rest of the body, or when one or more of the heart valves becomes stenotic or otherwise incompetent, blood can back up into the lungs, causing the lungs to become congested with fluid. If this backward flow occurs over an extended period of time, heart failure can result. Typical symptoms of heart failure include shortness of breath (dyspnea), fatigue, weakness, difficulty breathing when lying flat, and swelling of the legs, ankles or abdomen (edema). Causes of heart failure are related to various disorders including coronary artery disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction. The primary signs of congestive heart failure are: cardiomegaly (enlarged heart), tachypnea (rapid breathing; occurs in the case of left side failure) and hepatomegaly (enlarged liver; occurs in the case of right side failure).

As used herein, the term "hypertensive cardiomyopathy" refers to a weakened heart caused by the effects of hypertension (high blood pressure). Over time, uncontrolled hypertension causes weakness of the heart muscle. As hypertensive cardiomyopathy worsens, it can lead to congestive heart failure. Early symptoms of hypertensive cardiomyopathy include cough, weakness, and fatigue. Additional symptoms of hypertensive cardiomyopathy include leg swelling, weight gain, difficulty breathing when lying flat, increasing shortness of breath with activity, and waking in the middle of the night short of breath.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "polypeptide", "peptide", and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the terms "treating" or "treatment" or "alleviation" refers to therapeutic treatment, wherein the object is to prevent or slow down (lessen) the targeted pathologic condition or disorder. A subject is successfully "treated" for heart failure if, after receiving a therapeutic amount of the aromatic-cationic peptides according to the methods described herein, the subject shows observable and/or measurable reduction in or absence of one or more signs and symptoms of heart failure, such as, e.g., cardiac output, myocardial contractile force, cardiomegaly, tachonea, and/or hepahemogaly. It is also to be appreciated that the various modes of treatment or prevention of medical conditions as described are intended to mean "substantial", which includes total but also less than total treatment or prevention, and wherein some biologically or medically relevant result is achieved. Treating heart failure, as used herein, also refers to treating any one or more of the conditions underlying heart failure, including, without limitation, decreased cardiac contractility, abnormal diastolic compliance, reduced stroke volume, pulmonary congestion, and decreased cardiac output.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. As used herein, preventing heart failure includes preventing the initiation of heart failure, delaying the initiation of heart failure, preventing the progression or advancement of heart failure, slowing the progression or advancement of heart failure, delaying the progression or advancement of heart failure, and reversing the progression of heart failure from an advanced to a less advanced stage.

Aromatic-Cationic Peptides

The present technology relates to the treatment or prevention of heart failure and related conditions by administration of certain aromatic-cationic peptides. The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. As used herein, the term "amino acid" is used to refer to any organic molecule that contains at least one amino group and at least one carboxyl group. Typically, at least one amino group is at the α position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant or insensitive to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

Amino acid number and net positive charges ($3p_m \leq p + 1$)

| (r) | | | | | | | | | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| (r) | | | | | | | | | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys- Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t+1$, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | | | | | | | | | | | | | | | | | | | |
|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 |
| (a) 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

TABLE 4

Aromatic groups and net positive charges ($2a \leq p_t + 1$ or $a = p_t = 1$)

| ($p_t$) | | | | | | | | | | | | | | | | | | | |
|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 |
| (a) 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:
Lys-D-Arg-Tyr-NH$_2$
Phe-D-Arg-His
D-Tyr-Trp-Lys-NH$_2$
Trp-D-Lys-Tyr-Arg-NH$_2$
Tyr-His-D-Gly-Met
Phe-Arg-D-His-Asp
Tyr-D-Arg-Phe-Lys-Glu-NH$_2$
Met-Tyr-D-Lys-Phe-Arg
D-His-Glu-Lys-Tyr-D-Phe-Arg
Lys-D-Gln-Tyr-Arg-D-Phe-Trp-NH$_2$
Phe-D-Arg-Lys-Trp-Tyr-D-Arg-His
Gly-D-Phe-Lys-Tyr-His-D-Arg-Tyr-NH$_2$
Val-D-Lys-His-Tyr-D-Phe-Ser-Tyr-Arg-NH$_2$
Trp-Lys-Phe-D-Asp-Arg-Tyr-D-His-Lys
Lys-Trp-D-Tyr-Arg-Asn-Phe-Tyr-D-His-NH$_2$
Thr-Gly-Tyr-Arg-D-His-Phe-Trp-D-His-Lys
Asp-D-Trp-Lys-Tyr-D-His-Phe-Arg-D-Gly-Lys-NH$_2$
D-His-Lys-Tyr-D-Phe-Glu-D-Asp-D-His-D-Lys-Arg-Trp-NH$_2$
Ala-D-Phe-D-Arg-Tyr-Lys-D-Trp-His-D-Tyr-Gly-Phe
Tyr-D-His-Phe-D-Arg-Asp-Lys-D-Arg-His-Trp-D-His-Phe
Phe-Phe-D-Tyr-Arg-Glu-Asp-D-Lys-Arg-D-Arg-His-Phe-NH$_2$
Phe-Try-Lys-D-Arg-Trp-His-D-Lys-D-Lys-Glu-Arg-D-Tyr-Thr
Tyr-Asp-D-Lys-Tyr-Phe-D-Lys-D-Arg-Phe-Pro-D-Tyr-His-Lys
Glu-Arg-D-Lys-Tyr-D-Val-Phe-D-His-Trp-Arg-D-Gly-Tyr-Arg-D-Met-NH$_2$
Arg-D-Leu-D-Tyr-Phe-Lys-Glu-D-Lys-Arg-D-Trp-Lys-D-Phe-Tyr-D-Arg-Gly
D-Glu-Asp-Lys-D-Arg-D-His-Phe-Phe-D-Val-Tyr-Arg-Tyr-D-Tyr-Arg-His-Phe-NH$_2$
Asp-Arg-D-Phe-Cys-Phe-D-Arg-D-Lys-Tyr-Arg-D-Tyr-Trp-D-His-Tyr-D-Phe-Lys-Phe
His-Tyr-D-Arg-Trp-Lys-Phe-D-Asp-Ala-Arg-Cys-D-Tyr-His-Phe-D-Lys-Tyr-His-Ser-NH$_2$
Gly-Ala-Lys-Phe-D-Lys-Glu-Arg-Tyr-His-D-Arg-D-Arg-Asp-Tyr-Trp-D-His-Trp-His-D-Lys-Asp
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$ In one embodiment, the peptides have mu-opioid receptor agonist activity (i.e., they activate the mu-opioid receptor). Peptides which have mu-opioid receptor agonist activity are typically those peptides which have a tyrosine residue or a tyrosine derivative at the N-terminus (i.e., the first amino acid position). Suitable derivatives of tyrosine include 2'-methyltyrosine (Mmt); 2',6'-dimethyltyrosine (2'6'-Dmt); 3',5'-dimethyltyrosine (3'5'Dmt); N,2',6'-trimethyltyrosine (Tmt); and 2'-hydroxy-6'-methyltryosine (Hmt).

In one embodiment, a peptide that has mu-opioid receptor agonist activity has the formula Tyr-D-Arg-Phe-Lys-NH$_2$ (referred to herein as "SS-01"). SS-01 has a net positive charge of three, contributed by the amino acids tyrosine, arginine, and lysine and has two aromatic groups contributed by the amino acids phenylalanine and tyrosine. The tyrosine of SS-01 can be a modified derivative of tyrosine such as in 2',6'-dimethyltyrosine to produce the compound having the formula 2',6'-Dmt-D-Arg-Phe-Lys-NH$_2$ (referred to herein as "SS-02"). SS-02 has a molecular weight of 640 and carries a net three positive charge at physiological pH. SS-02 readily penetrates the plasma membrane of several mammalian cell types in an energy-independent manner (Zhao et al., *J. Pharmacol Exp Ther.*, 304:425-432, 2003).

Alternatively, in other instances, the aromatic-cationic peptide does not have mu-opioid receptor agonist activity. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$ (referred to herein as "SS-20"). Alternatively, the N-terminal phenylalanine can be a derivative of phenylalanine such as 2',6'-dimethyiphenylalanine (2'6'-Dmp). SS-01 containing 2',6'-dimethyiphenylalanine at amino acid position 1 has the formula 2',6'-Dmp-D-Arg-Phe-Lys-NH$_2$. In one embodiment, the amino acid sequence of SS-02 is rearranged such that Dmt is not at the N-terminus. An example of such an aromatic-cationic peptide that does not have mu-opioid receptor agonist activity has the formula D-Arg-2'6'-Dmt-Lys-Phe-NH$_2$.

Suitable substitution variants of the peptides listed herein include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

Examples of peptides that activate mu-opioid receptors include, but are not limited to, the aromatic-cationic peptides shown in Table 5.

TABLE 5

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| 2'6'Dmt | D-Arg | Phe | Lys | NH$_2$ |
| 2'6'Dmt | D-Arg | Phe | Lys-NH(CH$_2$)$_2$—NH-dns | NH$_2$ |
| 2'6'Dmt | D-Arg | Phe | Lys-NH(CH$_2$)$_2$—NH-atn | NH$_2$ |
| 2'6'Dmt | D-Arg | Phe | dnsLys | NH$_2$ |
| 2'6'Dmt | D-Cit | Phe | Lys | NH$_2$ |
| 2'6'Dmt | D-Cit | Phe | Ahp | NH$_2$ |
| 2'6'Dmt | D-Arg | Phe | Orn | NH$_2$ |
| 2'6'Dmt | D-Arg | Phe | Dab | NH$_2$ |
| 2'6'Dmt | D-Arg | Phe | Dap | NH$_2$ |
| 2'6'Dmt | D-Arg | Phe | Ahp(2-aminoheptanoic acid) | NH$_2$ |
| Bio-2'6'Dmt | D-Arg | Phe | Lys | NH$_2$ |
| 3'5'Dmt | D-Arg | Phe | Lys | NH$_2$ |
| 3'5'Dmt | D-Arg | Phe | Orn | NH$_2$ |
| 3'5'Dmt | D-Arg | Phe | Dab | NH$_2$ |
| 3'5'Dmt | D-Arg | Phe | Dap | NH$_2$ |
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2'6'Dmt | D-Arg | Tyr | Lys | NH$_2$ |
| 2'6'Dmt | D-Arg | Tyr | Orn | NH$_2$ |
| 2'6'Dmt | D-Arg | Tyr | Dab | NH$_2$ |

TABLE 5-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| 2'6'Dmt | D-Arg | Tyr | Dap | NH$_2$ |
| 2'6'Dmt | D-Arg | 2'6'Dmt | Lys | NH$_2$ |
| 2'6'Dmt | D-Arg | 2'6'Dmt | Orn | NH$_2$ |
| 2'6'Dmt | D-Arg | 2'6'Dmt | Dab | NH$_2$ |
| 2'6'Dmt | D-Arg | 2'6'Dmt | Dap | NH$_2$ |
| 3'5'Dmt | D-Arg | 3'5'Dmt | Arg | NH$_2$ |
| 3'5'Dmt | D-Arg | 3'5'Dmt | Lys | NH$_2$ |
| 3'5'Dmt | D-Arg | 3'5'Dmt | Orn | NH$_2$ |
| 3'5'Dmt | D-Arg | 3'5'Dmt | Dab | NH$_2$ |
| Tyr | D-Lys | Phe | Dap | NH$_2$ |
| Tyr | D-Lys | Phe | Arg | NH$_2$ |
| Tyr | D-Lys | Phe | Lys | NH$_2$ |
| Tyr | D-Lys | Phe | Orn | NH$_2$ |
| 2'6'Dmt | D-Lys | Phe | Dab | NH$_2$ |
| 2'6'Dmt | D-Lys | Phe | Dap | NH$_2$ |
| 2'6'Dmt | D-Lys | Phe | Arg | NH$_2$ |
| 2'6'Dmt | D-Lys | Phe | Lys | NH$_2$ |
| 3'5'Dmt | D-Lys | Phe | Orn | NH$_2$ |
| 3'5'Dmt | D-Lys | Phe | Dab | NH$_2$ |
| 3'5'Dmt | D-Lys | Phe | Dap | NH$_2$ |
| 3'5'Dmt | D-Lys | Phe | Arg | NH$_2$ |
| Tyr | D-Lys | Tyr | Lys | NH$_2$ |
| Tyr | D-Lys | Tyr | Orn | NH$_2$ |
| Tyr | D-Lys | Tyr | Dab | NH$_2$ |
| Tyr | D-Lys | Tyr | Dap | NH$_2$ |
| 2'6'Dmt | D-Lys | Tyr | Lys | NH$_2$ |
| 2'6'Dmt | D-Lys | Tyr | Orn | NH$_2$ |
| 2'6'Dmt | D-Lys | Tyr | Dab | NH$_2$ |
| 2'6'Dmt | D-Lys | Tyr | Dap | NH$_2$ |
| 2'6'Dmt | D-Lys | 2'6'Dmt | Lys | NH$_2$ |
| 2'6'Dmt | D-Lys | 2'6'Dmt | Orn | NH$_2$ |
| 2'6'Dmt | D-Lys | 2'6'Dmt | Dab | NH$_2$ |
| 2'6'Dmt | D-Lys | 2'6'Dmt | Dap | NH$_2$ |
| 2'6'Dmt | D-Arg | Phe | dnsDap | NH$_2$ |
| 2'6'Dmt | D-Arg | Phe | atnDap | NH$_2$ |
| 3'5'Dmt | D-Lys | 3'5'Dmt | Lys | NH$_2$ |
| 3'5'Dmt | D-Lys | 3'5'Dmt | Orn | NH$_2$ |
| 3'5'Dmt | D-Lys | 3'5'Dmt | Dab | NH$_2$ |
| 3'5'Dmt | D-Lys | 3'5'Dmt | Dap | NH$_2$ |
| Tyr | D-Lys | Phe | Arg | NH$_2$ |
| Tyr | D-Orn | Phe | Arg | NH$_2$ |
| Tyr | D-Dab | Phe | Arg | NH$_2$ |
| Tyr | D-Dap | Phe | Arg | NH$_2$ |
| 2'6'Dmt | D-Arg | Phe | Arg | NH$_2$ |
| 2'6'Dmt | D-Lys | Phe | Arg | NH$_2$ |
| 2'6'Dmt | D-Orn | Phe | Arg | NH$_2$ |
| 2'6'Dmt | D-Dab | Phe | Arg | NH$_2$ |
| 3'5'Dmt | D-Dap | Phe | Arg | NH$_2$ |
| 3'5'Dmt | D-Arg | Phe | Arg | NH$_2$ |
| 3'5'Dmt | D-Lys | Phe | Arg | NH$_2$ |
| 3'5'Dmt | D-Orn | Phe | Arg | NH$_2$ |
| Tyr | D-Lys | Tyr | Arg | NH$_2$ |
| Tyr | D-Orn | Tyr | Arg | NH$_2$ |
| Tyr | D-Dab | Tyr | Arg | NH$_2$ |
| Tyr | D-Dap | Tyr | Arg | NH$_2$ |
| 2'6'Dmt | D-Arg | 2'6'Dmt | Arg | NH$_2$ |
| 2'6'Dmt | D-Lys | 2'6'Dmt | Arg | NH$_2$ |
| 2'6'Dmt | D-Orn | 2'6'Dmt | Arg | NH$_2$ |
| 2'6'Dmt | D-Dab | 2'6'Dmt | Arg | NH$_2$ |
| 3'5'Dmt | D-Dap | 3'5'Dmt | Arg | NH$_2$ |
| 3'5'Dmt | D-Arg | 3'5'Dmt | Arg | NH$_2$ |
| 3'5'Dmt | D-Lys | 3'5'Dmt | Arg | NH$_2$ |
| 3'5'Dmt | D-Orn | 3'5'Dmt | Arg | NH$_2$ |
| Mmt | D-Arg | Phe | Lys | NH$_2$ |
| Mmt | D-Arg | Phe | Orn | NH$_2$ |
| Mmt | D-Arg | Phe | Dab | NH$_2$ |
| Mmt | D-Arg | Phe | Dap | NH$_2$ |
| Tmt | D-Arg | Phe | Lys | NH$_2$ |
| Tmt | D-Arg | Phe | Orn | NH$_2$ |
| Tmt | D-Arg | Phe | Dab | NH$_2$ |
| Tmt | D-Arg | Phe | Dap | NH$_2$ |
| Hmt | D-Arg | Phe | Lys | NH$_2$ |
| Hmt | D-Arg | Phe | Orn | NH$_2$ |
| Hmt | D-Arg | Phe | Dab | NH$_2$ |
| Hmt | D-Arg | Phe | Dap | NH$_2$ |

TABLE 5-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Mmt | D-Lys | Phe | Lys | NH$_2$ |
| Mmt | D-Lys | Phe | Orn | NH$_2$ |
| Mmt | D-Lys | Phe | Dab | NH$_2$ |
| Mmt | D-Lys | Phe | Dap | NH$_2$ |
| Mmt | D-Lys | Phe | Arg | NH$_2$ |
| Tmt | D-Lys | Phe | Lys | NH$_2$ |
| Tmt | D-Lys | Phe | Orn | NH$_2$ |
| Tmt | D-Lys | Phe | Dab | NH$_2$ |
| Tmt | D-Lys | Phe | Dap | NH$_2$ |
| Tmt | D-Lys | Phe | Arg | NH$_2$ |
| Hmt | D-Lys | Phe | Lys | NH$_2$ |
| Hmt | D-Lys | Phe | Orn | NH$_2$ |
| Hmt | D-Lys | Phe | Dab | NH$_2$ |
| Hmt | D-Lys | Phe | Dap | NH$_2$ |
| Hmt | D-Lys | Phe | Arg | NH$_2$ |
| Mmt | D-Lys | Phe | Arg | NH$_2$ |
| Mmt | D-Orn | Phe | Arg | NH$_2$ |
| Mmt | D-Dab | Phe | Arg | NH$_2$ |
| Mmt | D-Dap | Phe | Arg | NH$_2$ |
| Mmt | D-Arg | Phe | Arg | NH$_2$ |
| Tmt | D-Lys | Phe | Arg | NH$_2$ |
| Tmt | D-Orn | Phe | Arg | NH$_2$ |
| Tmt | D-Dab | Phe | Arg | NH$_2$ |
| Tmt | D-Dap | Phe | Arg | NH$_2$ |
| Tmt | D-Arg | Phe | Arg | NH$_2$ |
| Hmt | D-Lys | Phe | Arg | NH$_2$ |
| Hmt | D-Orn | Phe | Arg | NH$_2$ |
| Hmt | D-Dab | Phe | Arg | NH$_2$ |
| Hmt | D-Dap | Phe | Arg | NH$_2$ |
| Hmt | D-Arg | Phe | Arg | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides that do not activate mu-opioid receptors include, but are not limited to, the aromatic-cationic peptides shown in Table 6.

TABLE 6

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | NH$_2$ |
| D-Arg | Dmt | Phe | Lys | NH$_2$ |
| D-Arg | Phe | Lys | Dmt | NH$_2$ |
| D-Arg | Phe | Dmt | Lys | NH$_2$ |
| D-Arg | Lys | Dmt | Phe | NH$_2$ |
| D-Arg | Lys | Phe | Dmt | NH$_2$ |
| Phe | Lys | Dmt | D-Arg | NH$_2$ |
| Phe | Lys | D-Arg | Dmt | NH$_2$ |
| Phe | D-Arg | Phe | Lys | NH$_2$ |
| Phe | D-Arg | Dmt | Lys | NH$_2$ |
| Phe | D-Arg | Lys | Dmt | NH$_2$ |
| Phe | Dmt | D-Arg | Lys | NH$_2$ |
| Phe | Dmt | Lys | D-Arg | NH$_2$ |
| Lys | Phe | D-Arg | Dmt | NH$_2$ |
| Lys | Phe | Dmt | D-Arg | NH$_2$ |
| Lys | Dmt | D-Arg | Phe | NH$_2$ |
| Lys | Dmt | Phe | D-Arg | NH$_2$ |
| Lys | D-Arg | Phe | Dmt | NH$_2$ |
| Lys | D-Arg | Dmt | Phe | NH$_2$ |
| D-Arg | Dmt | D-Arg | Phe | NH$_2$ |
| D-Arg | Dmt | D-Arg | Dmt | NH$_2$ |
| D-Arg | Dmt | D-Arg | Tyr | NH$_2$ |
| D-Arg | Dmt | D-Arg | Trp | NH$_2$ |
| Trp | D-Arg | Phe | Lys | NH$_2$ |
| Trp | D-Arg | Tyr | Lys | NH$_2$ |
| Trp | D-Arg | Trp | Lys | NH$_2$ |
| Trp | D-Arg | Dmt | Lys | NH$_2$ |
| D-Arg | Trp | Lys | Phe | NH$_2$ |
| D-Arg | Trp | Phe | Lys | NH$_2$ |
| D-Arg | Trp | Lys | Dmt | NH$_2$ |
| D-Arg | Trp | Dmt | Lys | NH$_2$ |
| D-Arg | Lys | Trp | Phe | NH$_2$ |
| D-Arg | Lys | Trp | Dmt | NH$_2$ |
| Cha | D-Arg | Phe | Lys | NH$_2$ |
| Ala | D-Arg | Phe | Lys | NH$_2$ |

Cha = cyclohexyl alanine

The amino acids of the peptides shown in Table 5 and 6 may be in either the L- or the D-configuration.

The peptides may be synthesized by any of the methods well known in the art. Suitable methods for chemically synthesizing the protein include, for example, those described by Stuart and Young in *Solid Phase Peptide*

*Synthesis*, Second Edition, Pierce Chemical Company (1984), and in *Methods Enzymol.*, 289, Academic Press, Inc, New York (1997).

Prophylactic and Therapeutic Uses of Aromatic-Cationic Peptides.

General. The aromatic-cationic peptides described herein are useful to prevent or treat disease. Specifically, the disclosure provides for both prophylactic and therapeutic methods of treating a subject having or at risk of (susceptible to) heart failure. Accordingly, the present methods provide for the prevention and/or treatment of heart failure in a subject by administering an effective amount of an aromatic-cationic peptide to a subject in need thereof. See Tsutsui et al. "Mitochondrial oxidative stress, DNA damage, and heart failure." *Antioxidants and Redox Signaling.* 8(9): 1737-1744 (2006).

Therapeutic Methods. One aspect of the technology includes methods of treating heart failure in a subject for therapeutic purposes. In therapeutic applications, compositions or medicaments are administered to a subject suspected of, or already suffering from such a disease in an amount sufficient to cure, or at least partially arrest, the symptoms of the disease, including its complications and intermediate pathological phenotypes in development of the disease. As such, the invention provides methods of treating an individual afflicted with heart failure.

Subjects suffering from heart failure can be identified by any or a combination of diagnostic or prognostic assays known in the art. For example, typical symptoms of heart failure include shortness of breath (dyspnea), fatigue, weakness, difficulty breathing when lying flat, and swelling of the legs, ankles or abdomen (edema). The subject may also be suffering from other disorders including coronary artery disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction. The primary signs of congestive heart failure are: cardiomegaly (enlarged heart), tachypnea (rapid breathing; occurs in the case of left side failure) and hepatomegaly (enlarged liver; occurs in the case of right side failure). Acute myocardial infarction ("AMI") due to obstruction of a coronary artery is a common initiating event that can lead ultimately to heart failure. However, a subject that has AMI does not necessarily develop heart failure. Likewise, subjects that suffer from heart failure did not necessarily suffer from an AMI.

In one aspect, the present disclosure provides a method of treating hypertensive cardiomyopathy by administering an effective amount of an aromatic-cationic peptide to a subject in need thereof. As hypertensive cardiomyopathy worsens, it can lead to congestive heart failure. Subjects suffering from hypertensive cardiomyopathy can be identified by any or a combination of diagnostic or prognostic assays known in the art. example, typical symptoms of hypertensive cardiomyopathy include hypertension (high blood pressure), cough, weakness, and fatigue. Additional symptoms of hypertensive cardiomyopathy include leg swelling, weight gain, difficulty breathing when lying flat, increasing shortness of breath with activity, and waking in the middle of the night short of breath.

Prophylactic Methods. In one aspect, the invention provides a method for preventing, in a subject, heart failure by administering to the subject an aromatic-cationic peptide that prevents the initiation or progression of the infection. Subjects at risk for heart failure can be identified by, e.g., any or a combination of diagnostic or prognostic assays as described herein. In prophylactic applications, pharmaceutical compositions or medicaments of aromatic-cationic peptides are administered to a subject susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic aromatic-cationic can occur prior to the manifestation of symptoms characteristic of the aberrancy, such that a disease or disorder is prevented or, alternatively, delayed in its progression. The appropriate compound can be determined based on screening assays described above.

Determination of the Biological Effect of the Aromatic-Cationic Peptide-Based Therapeutic. In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect in preventing or treating heart failure. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

HF has been induced in different species with volume overload, pressure overload, fast pacing, myocardial ischemia, cardiotoxic drugs, or genetically modified models. Models using pressure overload have been most commonly used. Hypertension is associated with an increased risk for the development of HF. In one mouse model, angiotensin II (Ang II) increases blood pressure and induces cardiomyocyte hypertrophy, increased cardiac fibrosis, and impaired cardiomyocyte relaxation. Infusion of angiotensin to mice by mini osmotic pump increases systolic and diastolic blood pressure, increases heart weight and left ventricular thickness (LVMI), and impaired myocardial performance index (MPI).

In a second illustrative mouse model, sustained high level expression of Gαq can lead to marked myocyte apoptosis, resulting in cardiac hypertrophy and heart failure by 16 weeks of age (D'Angelo et al., 1998). The β-adrenergic receptors (PARs) are primarily coupled to the heterotrimeric G protein, Gs, to stimulate adenylyl cyclase activity. This association generates intracellular cAMP and protein kinase A activation, which regulate cardiac contractility and heart rate. Overexpression of Gαq leads to decreased responsiveness to β-adrenergic agonists and results in HF.

Experimental constriction of the aorta by surgical ligation is also widely used as a model of HF. Transaortic constriction (TAC) results in pressure overload induced HF, with increase in left ventricular (LV) mass. TAC is performed as described by Tamavski O et al. (2004) using a 7-0 silk double-knot suture to constrict the ascending aorta. After TAC, mice develop HF within a period of 4 weeks.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides are administered to the subject in effective amounts (i.e., amounts that have desired therapeutic effect). The dose and dosage regimen will depend upon the degree of the infection in the subject, the characteristics of the particular aromatic-cationic peptide used, e.g., its therapeutic index, the subject, and the subject's history.

The effective amount may be determined during pre-clinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The aromatic-cationic peptides described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminctetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed my iontophoresis.

A therapeutic protein or peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, clastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100: 63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.001-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a preferred embodiment, the mammal is a human.

Combination Therapy with an Aromatic-Cationic Peptide and Other Therapeutic Agents In some embodiments, the aromatic-cationic peptides may be combined with one or more additional agents for the prevention or treatment of heart failure. Drug treatment for heart failure typically involves diuretics, ACE inhibitors, digoxin (also called digitalis), calcium channel blockers, and beta-blockers. In mild cases, thiazide diuretics, such as hydrochlorothiazide at 25-50 mg/day or chlorothiazide at 250-500 mg/day, are useful. However, supplemental potassium chloride may be needed, since chronic diuresis causes hypokalemis alkalosis. Moreover, thiazide diuretics usually are not effective in patients with advanced symptoms of heart failure. Typical doses of ACE inhibitors include captopril at 25-50 mg/day and quinapril at 10 mg/day.

In one embodiment, the aromatic-cationic peptide is combined with an adrenergic beta-2 agonist. An "adrenergic beta-2 agonist" refers to adrenergic beta-2 agonists and analogues and derivatives thereof, including, for example, natural or synthetic functional variants which have adrenergic beta-2 agonist biological activity, as well as fragments of an adrenergic beta-2 agonist having adrenergic beta-2 agonist biological activity. The term "adrenergic beta-2 agonist biological activity" refers to activity that mimics the effects of adrenaline and noradrenaline in a subject and which improves myocardial contractility in a patient having heart failure. Commonly known adrenergic beta-2 agonists include, but are not limited to, clenbuterol, albuterol, formeoterol, levalbuterol, metaproterenol, pirbuterol, salmeterol, and terbutaline.

In one embodiment, the aromatic-cationic peptide is combined with an adrenergic beta-1 antagonist. Adrenergic beta-1 antagonists and adrenergic beta-1 blockers refer to adrenergic beta-1 antagonists and analogues and derivatives thereof, including, for example, natural or synthetic functional variants which have adrenergic beta-1 antagonist biological activity, as well as fragments of an adrenergic beta-1 antagonist having adrenergic beta-1 antagonist biological activity. Adrenergic beta-1 antagonist biological activity refers to activity that blocks the effects of adrenaline on beta receptors. Connonly known adrenergic beta-1 antagonists include, but are not limited to, acebutolol, atenolol, betaxolol, bisoprolol, esmolol, and metoprolol.

Clenbuterol, for example, is available under numerous brand names including Spiropent® (Boehinger Ingelheim), Broncodil® (Von Boch I), Broncoterol® (Quimedical PT), Cesbron® (Fidelis PT), and Clenbuter® (Biomedica Foscama). Similarly, methods of preparing adrenergic beta-1 antagonists such as metoprolol and their analogues and derivatives are well-known in the art. Metoprolol, in particular, is commercially available under the brand names Lopressor® (metoprolol tartate) manufactured by Novartis Pharmaceuticals Corporation, One Health Plaza, East Hanover, N.J. 07936-1080. Generic versions of Lopressor® are also available from Mylan Laboratories Inc., 1500 Corporate Drive, Suite 400, Canonsburg, Pa. 15317; and Watson Pharmaceuticals, Inc., 360 Mt. Kemble Ave. Morristown, N.J. 07962. Metoprolol is also commercially available under the brand name Toprol XL®, manufactured by Astra Zeneca, LP.

In one embodiment, an additional therapeutic agent is administered to a subject in combination with an aromatic cationic peptide, such that a synergistic therapeutic effect is produced. A "synergistic therapeutic effect" refers to a greater-than-additive therapeutic effect which is produced by a combination of two therapeutic agents, and which exceeds that which would otherwise result from individual administration of either therapeutic agent alone. Therefore, lower doses of one or both of the therapeutic agents may be used in treating heart failure, resulting in increased therapeutic efficacy and decreased side-effects.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

The present invention is further illustrated by the following examples, which should not be construed as limiting in any way.

Example 1—Effects of Aromatic-Cationic Peptides in Mouse Models of Heart Failure In this Example, the effect of reducing mitochondrial oxidative stress by the mitochondrial-targeted antioxidant peptide (SS-31) in hypertensive cardiomyopathy and heart failure was investigated. The mitochondrial targeted antioxidant peptide SS-31 was used to determine the role of NADPH oxidase and mitochondria in Angiotensin II (Ang II)-induced cardiomyopathy, as well as in Gαq overexpressing mice with heart failure.

Methods

Neonatal mouse cardiomyocyte culture and flow cytometry. Ventricles from mouse neonates younger than 72 hours were dissected, minced, and enzymatically digested with Blendzyme 4 (45 µg/ml, Roche). After enzymatic digestion, cardiomyocytes were enriched using differential pre-plating for 2 hours, then seeded on fibronectin-coated culture dishes for 24 hours in DMEM (Gibco), with 20% Fetal Bovine Serum (Sigma) and 25 µM Arabinosylcytosine (Sigma). Cardiomyocytes were stimulated with Angiotensin II (1 µM) for 3 hours in serum-free DMEM containing 0.5% insulin transferrin-selenium (Sigma), 2 mM glutamine, and 1 mg/ml of BSA. Cardiomyocytes were simultaneously treated with either of the following: SS-31 (1 nM), N-acetyl cysteine (NAC: 0.5 mM), or PBS control. To measure mitochondrial superoxide concentration, Mitosox (5 µM) was incubated for 30 min at 37° C. to load cardiomyocytes, followed by 2 washes, with Hanks Balanced Salt Solution. Samples were analyzed using excitation/emission of 488/625 nm by flow cytometry. Flow data was analyzed using FCS Express (De Novo Software, Los Angeles, CA), and presented as histogram distributions of Mitosox fluorescence intensity.

Mouse experiments, drug delivery, echocardiography and blood pressure measurement. All animal experiments were approved by the University of Washington Institutional Animal Care and Use Committee. C57BL6 mice were housed in a barrier specific pathogen-free facility. Six to ten mice were included in each experimental group (Saline, Ang II, Ang II+SS-31, WT, Gαq, Gαq+SS-31). A pressor dose of Ang II (1.1 mg/kg/d) was continuously administered for 4 weeks using subcutaneous Alzet 1004 osmotic minipumps, with or without addition of SS-31 (3 mg/kg/d). Echocardiography was performed at baseline and after 4 weeks of pump implantation using a Siemens Acuson CV-70 equipped with a 13 MHz probe. Under 0.5% isoflurane to reduce agitation, standard M-mode, conventional and Tissue Doppler images were taken, and functional calculations were performed according to American Society of Echocardiography guidelines. MPI was calculated as the ratio of the sum of isovolemic contraction and relaxation time to LV ejection time. An increase in MPI is an indication that a greater fraction of systole is spent to cope with the pressure changes during the isovolemic phases. As a reference for SS-31 peptide effect in Ang II treated mice, a genetic mouse model of Rosa-26 inducible-mCAT was included, in which mitochondrial catalase was overexpressed two weeks before Ang II treatment.

Blood pressure was measured in a separate group of mice by telemetry using an intravascular catheter PA-C10 (DSI, MN), in which measurement was performed every three hours starting from 2 days before pump placement until 2 days after Ang pump placement. After this time, a new pump loaded with Ang II+SS-31 was inserted, followed by another 2 days of recording to see if SS-31 had an effect on blood pressure.

Quantitative Pathology. Ventricular tissues were cut into transverse slices, and subsequently embedded with paraffin, sectioned, and subjected to Masson Trichrome staining. Quantitative analysis of fibrosis was performed by measuring the percentage of blue-staining fibrotic tissue relative to the total cross-sectional area of the ventricles.

Measurement of mitochondrial protein carbonyl groups. For mitochondrial protein extraction, ventricular tissues were homogenized in mitochondrial isolation buffer (1 mM EGTA, 10 mM HEPES, 250 mM sucrose, 10 mM Tris-HCl, pH 7.4). The lysates were centrifuged for 7 min at 800 g in 4° C. The supernatants were then centrifuged for 30 min at 4000 g in 4° C. The crude mitochondria pellets were resuspended in small volume of mitochondrial isolation buffer, sonicated on ice to disrupt the membrane, and treated with 1% streptomycin sulfate to precipitate mitochondrial nucleic acids. The OxiSelect™ Protein Carbonyl ELISA Kit (Cell Biolabs) was used to analyze 1 µg of protein sample per assay. The ELISA was performed according to the instruction manual, with slight modification. Briefly, protein samples were reacted with dinitrophenylhydrazine (DNPH) and probed with anti-DNPH antibody, followed by HRP conjugated secondary antibody. The anti-DNPH antibody and HRP conjugated secondary antibody concentrations were 1:2500 and 1:4000, respectively.

Quantitative PCR. Gene expression was quantified by quantitative real time PCR using an Applied Biosystems 7900 themocycler with Taqman Gene Expression Assays on Demand, which included: PGC1-α (Mm00731216), TFAM (Mm00447485), NRF-1 (Mm00447996), NRF-2 (Mm00487471), Collagen 1a2 (Mm00483937), and ANP (Mm01255747). Expression assays were normalized to 18S RNA.

NADPH Oxidase activity. The NADPH oxidase assay was performed as described elsewhere. In brief, 10 g of ventricular protein extract was incubated with dihydroethidium (DHE, 10 µM), sperm DNA (1.25 µg/ml), and NADPH (50 µM) in PBS/DTPA (containing 100 µM DTPA), The assay was incubated at 37° C. in the dark for 30 min and the fluorescence was detected using excitation/emission of 490/580 nm.

Western Immunoblots. Cardiac protein extracts were prepared by homogenization in lysis buffer containing protease and phosphatase inhibitors on ice (1.5 mM KCl, 50 mM Tris HCl, 0.125% Sodium deoxycholate, 0.375% Triton X 100, 0.15% NP40, 3 mM EDTA). The samples were sonicated and centrifuged at 10,000 g for 15 min in 4° C. The supernatant was collected and the concentration was determined using a BCA assay (Pierce Thermo Scientific, Rockford, IL). Total protein (25 μg) was separated on NuPAGE 4-12% Bis-Tris gel (Invitrogen) and transferred to 0.45 μm PVDF membrane (Millipore), and then blocked in 5% non-fat dry milk in Tris-buffer solution with 0.1% Tween-20 for 1 hour. Primary antibodies were incubated overnight, and secondary antibodies were incubated for 1 hour. The primary antibodies included: rabbit monoclonal anti-cleaved caspase-3 (Cell Signaling), mouse monoclonal anti-GAPDH (Millipore), rabbit polyclonal phospho-p38 MAP kinase (Cell Signaling), and mouse monoclonal anti-p38 (Santa Cruz Biotechnology). The enhanced chemiluminescence method (Thermo Scientific) was used for detection. Image Quant ver.2.0 was used to quantified the relative band density as a ratio to GAPDH (internal control). All samples were normalized to the same cardiac protein sample.

Statistical Analysis. All data are presented as mean±SEM. Comparisons between two groups are performed using Student t-tests. One-way ANOVA was used to compare differences among multiple groups, followed by Tukey post-hoc test for significance. $P<0.05$ were considered significant.

Results

Ang-II increased mitochondrial ROS in neonatal cardiomyoctyes, which was alleviated by mitochondrial antioxidant peptide SS-31. Flow cytometry analysis demonstrated that Angiotensin II increased Mitosox fluorescence (an indicator of mitochondrial superoxide) by approximately 2-fold in neonatal cardiomyocytes. Treatment with N-acetyl cysteine (NAC), a non-targeted antioxidant drug, did not show any effect on the level of mitochondrial ROS after Ang II. In contrast, SS-31 reduced Ang II-induced mitosox fluorescence to the level similar to that of saline treated cardiomyocytes (FIG. 1). These results indicated that Ang II induced mitochondrial oxidative stress in cardiomyocytes that could only be alleviated by a mitochondrial targeted antioxidant.

Figures 2A, 2B:
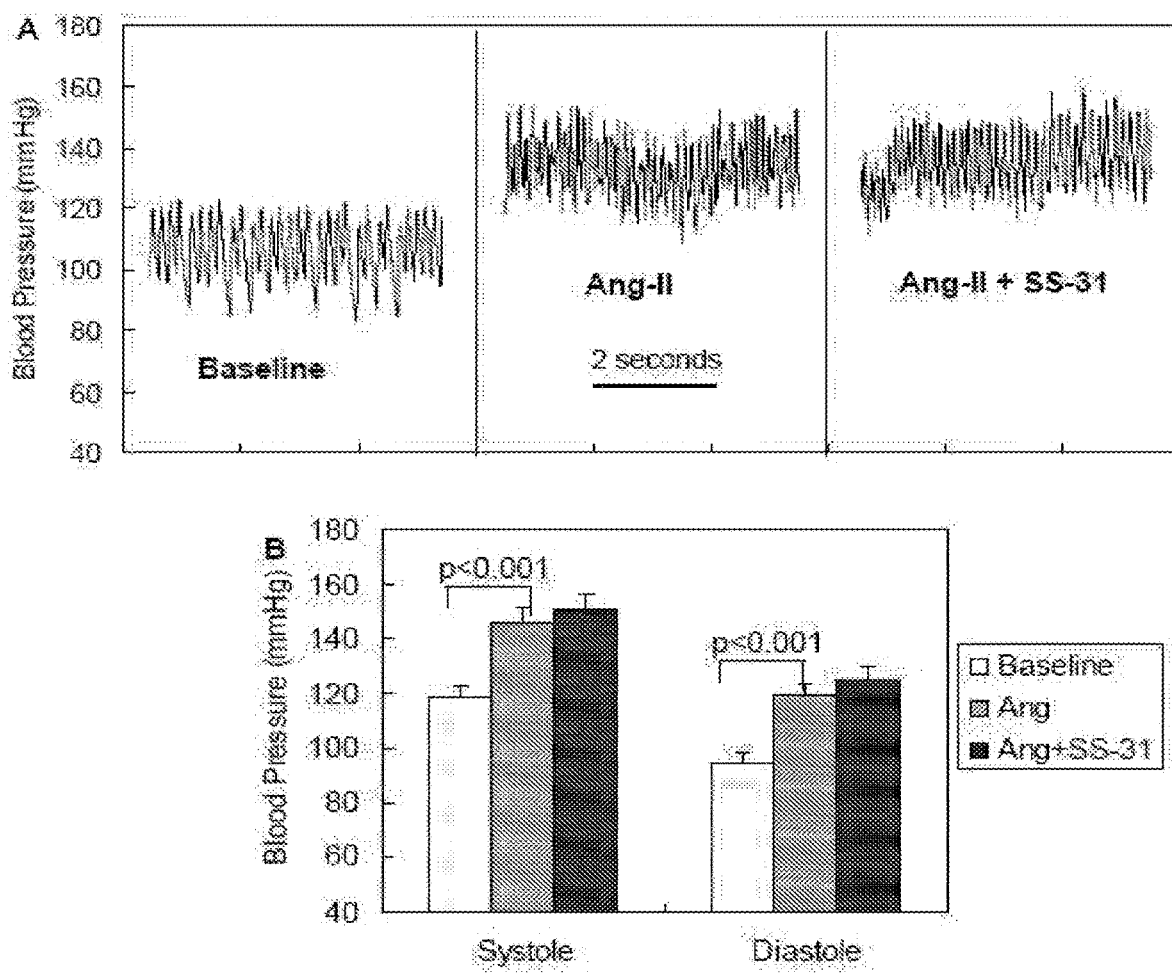
FIGS. 2A and 2B are a series of charts showing the effects of SS-31 on blood pressure after a pressor dose of Ang II.

SS-31 peptide ameliorates Ang-II induced cardiomyopathy despite the absence of blood pressure lowering effect. To recapitulate hypertensive cardiomyopathy, a pressor dose of Ang 1 (1.1 mg/kg/d) was administered for 4 weeks via subcutaneous continuous delivery with Alzet 1004 osmotic minipumps. As shown in FIGS. 2A and 2B, intravascular telemetry revealed that this dose of Ang II significantly increased systolic and diastolic blood pressure by 25-28 mm Hg above baseline (BP: 118.8±4.0/94.5±3.5 mm Hg at baseline vs. 146.0-5.6/119.3±4.0 mm Hg after Ang II, p<0.001). Simultaneous administration of SS-31 (3 mg/kg/d) did not show any effect on blood pressure (FIG. 2).

Figures 3A, 3B, 3C, 3D:
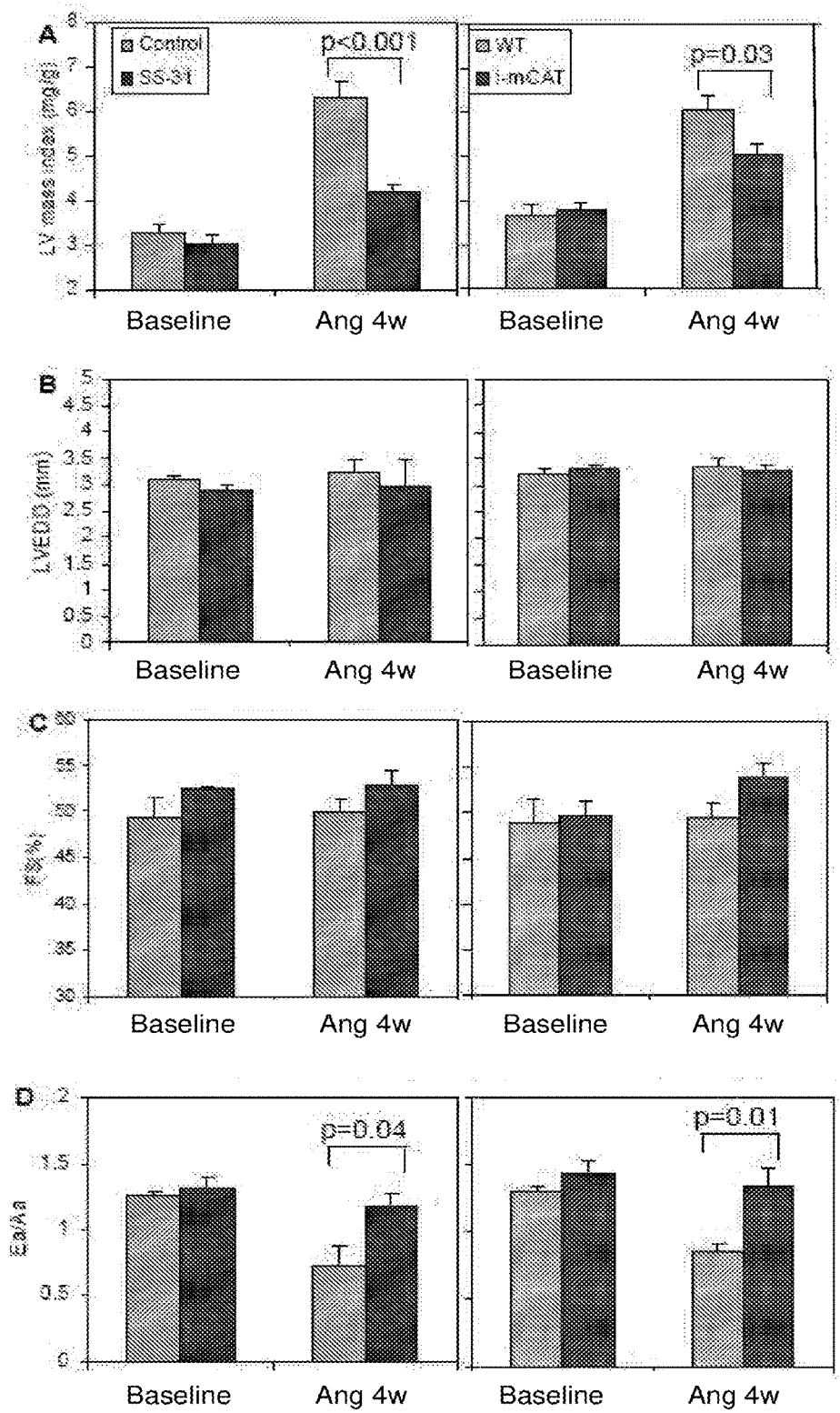
FIGS. 3A-3D are a series of charts showing that SS-31 ameliorates Ang-II-induced cardiac hypertrophy and diastolic dysfunction.
Figures 4A, 4B, 4C, 4D, 4E:
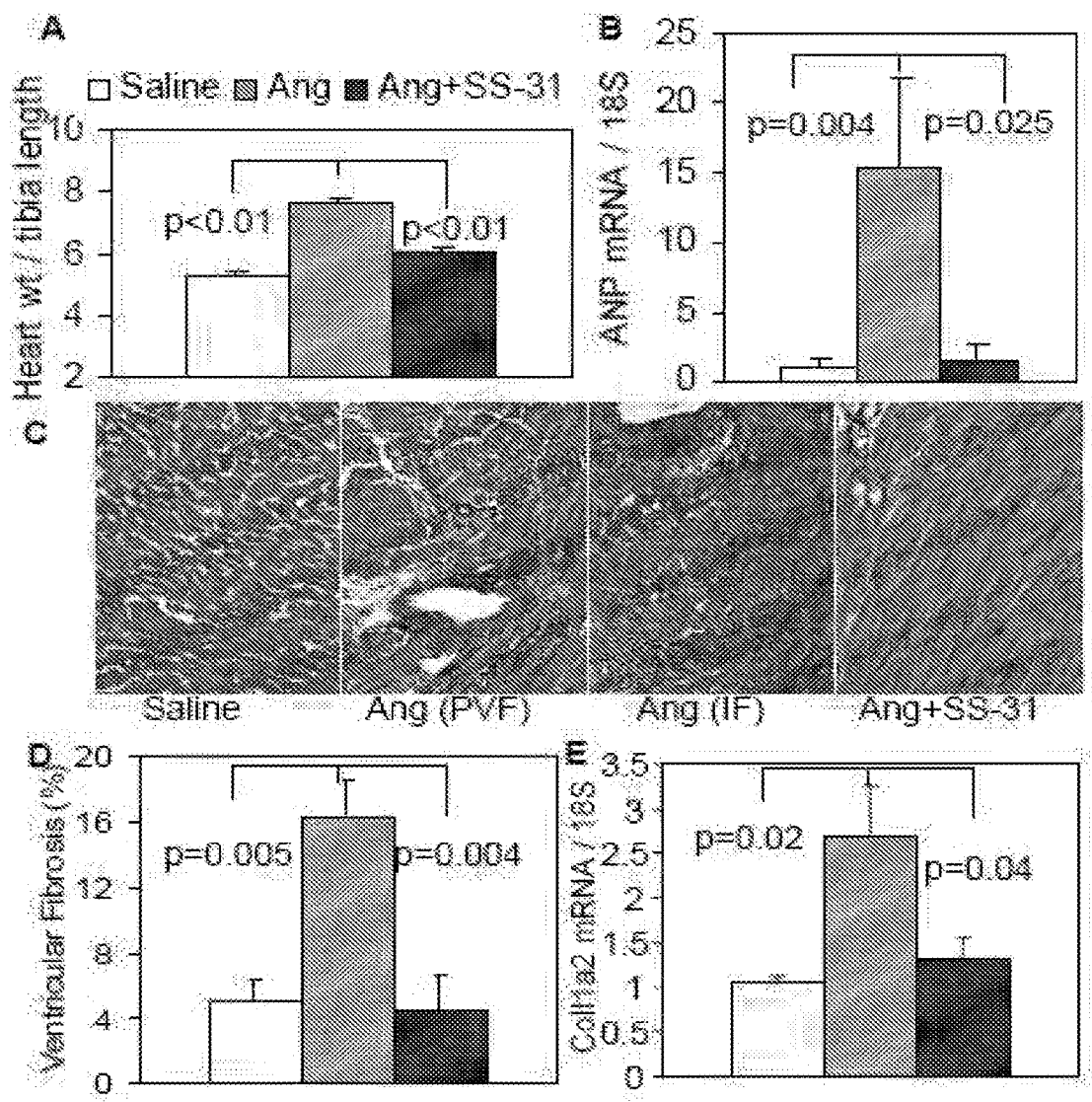
FIGS. 4A-4E are a series of charts showing SS-31 attenuates Ang-II induced cardiac hypertrophy and fibrosis.

After 4 weeks of Ang II, echocardiography revealed an approximately 2-fold increase in left ventricular mass index (LVMI) compared with baseline (FIG. 3A), no change in LV end diastolic diameter (LVEDD, FIG. 3B) or systolic function as measured by fractional shortening (FS, FIG. 3C), and ~35% decline in Ea/Aa, an indicator of diastolic function (FIG. 3D). Simultaneous administration of SS-31 significantly ameliorated Ang II induced cardiac hypertrophy and diastolic dysfunction, with 33% reduction of LVMI (Ang: 6.32±0.39 mg/g vs. Ang+SS-31: 4.21±0.17 mg/g, p=0.001, FIG. 3A left panel) and 38% better preservation of Ea/Aa (Ang: 0.723±0.15 vs. Ang+SS-31: 1.17±0.11, p=0.04, FIG. 3D left panel). These effects were comparable to the beneficial effects of catalase targeted to mitochondria (i-mCAT), in which induction of mitochondrial catalase two weeks before Ang II treatment conferred protection against Ang II induced cardiac hypertrophy and diastolic dysfunction (FIG. 3A-D, right panels). FIG. 4A demonstrated that Ang 11 increased heart weights by 45% above those of saline treated control hearts (5.3±0.18 in saline vs. 7.69±0.20 in Ang, p<0.001) and SS-31 reduced heart weights to 6.05±0.135 mg/mm (p<0.01 compared with Ang alone). The phenotype of cardiac hypertrophy was confirmed by quantitative PCR for atrial natriuretic peptide (ANP), a fetal gene known to be reactivated during hypertrophy. Ang II induced ~15 fold increased ANP gene expression, and this was almost completely protected by SS-31 (FIG. 4B).

The cardiac pathology was examined by Masson trichrome staining, which demonstrated perivascular fibrosis and interstitial fibrosis after 4 weeks of Ang II (FIG. 4C). Quantitative image analysis of ventricular fibrosis (blue staining on trichrome) showed that Ang II significantly increase ventricular fibrosis by greater than 3 fold, which was fully attenuated by SS-31 (FIG. 4D). The increase in cardiac fibrosis was confirmed by quantitative PCR of the procollagen 1a2 gene, the main component of fibrosis. As shown in FIG. 4E, Ang II increased Coll1a2 gene expression by ~2.5 fold, which was almost fully attenuated by SS-31 administration.

Ang H induced mitochondrial protein oxidative damage and signaling for mitochondrial biogenesis. Consistent with the finding that Ang II induced mitochondrial ROS in cardiomyocytes (FIG. 1), chronic administration of Ang 11 for 4 weeks significantly increased ventricular mitochondrial protein carbonyl content, which is an indicator of protein oxidative damage (p=0.03, FIG. 5A). Mitochondrial targeted antioxidant SS-31 significantly reduced cardiac mitochondrial protein carbonyls (p=0.02, FIG. 5A).

Figures 5A, 5B:
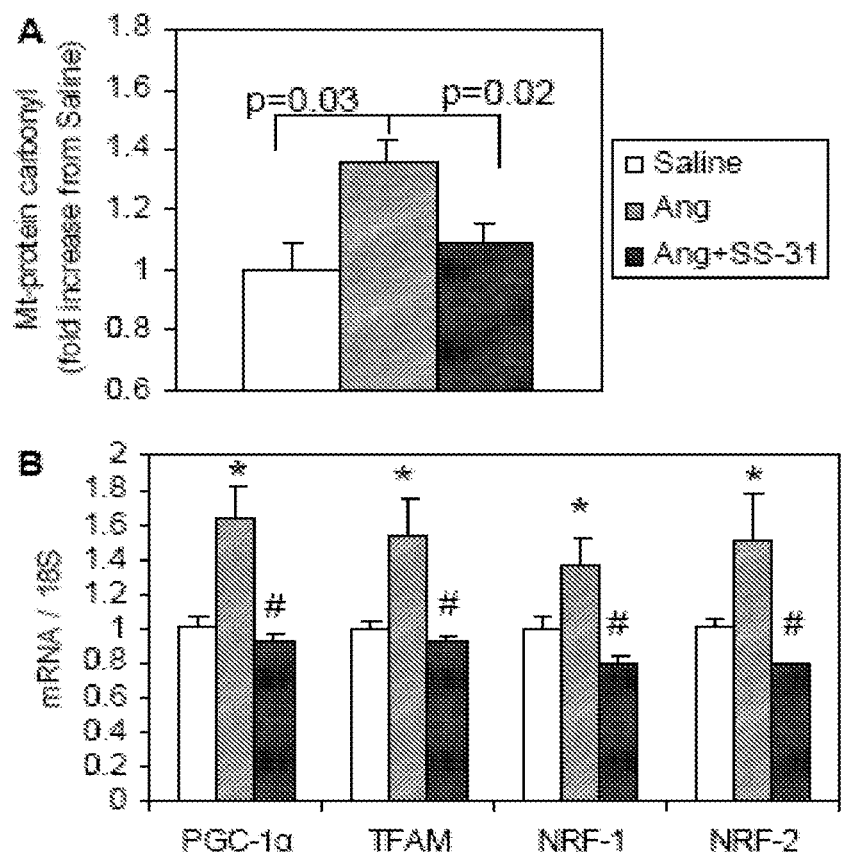
FIGS. 5A and 5B are a series of charts showing mitochondrial protein carbonyl and signaling for mitochondrial biogenesis increased after 4 weeks of Ang II treatment, which was prevented by SS-31.

Peroxisome proliferator-activated receptor gamma co-activator (PGC-1α) has been shown to be a master regulator of mitochondrial biogenesis, regulating nuclear respiratory factors (NRFs) and mitochondrial transcription factor A (TFAM), which transcribe nuclear DNA and mitochondrial DNA encoded mitochondrial proteins, respectively. As ROS induced mitochondrial damage has been shown to upregulate signaling for mitochondrial biogenesis, it was demonstrated that Ang II also induced the expression of PGC-1α and its downstream target genes, including TFAM, NRF-1 and NRF-2 (FIG. 5B). The mitochondrial antioxidant SS-31 was found to fully prevent the upregulation of PGC-1α and all the downstream target genes after 4 weeks of Ang II (p<0.05 for all, FIG. 5B).

Figures 6A, 6B, 6C:
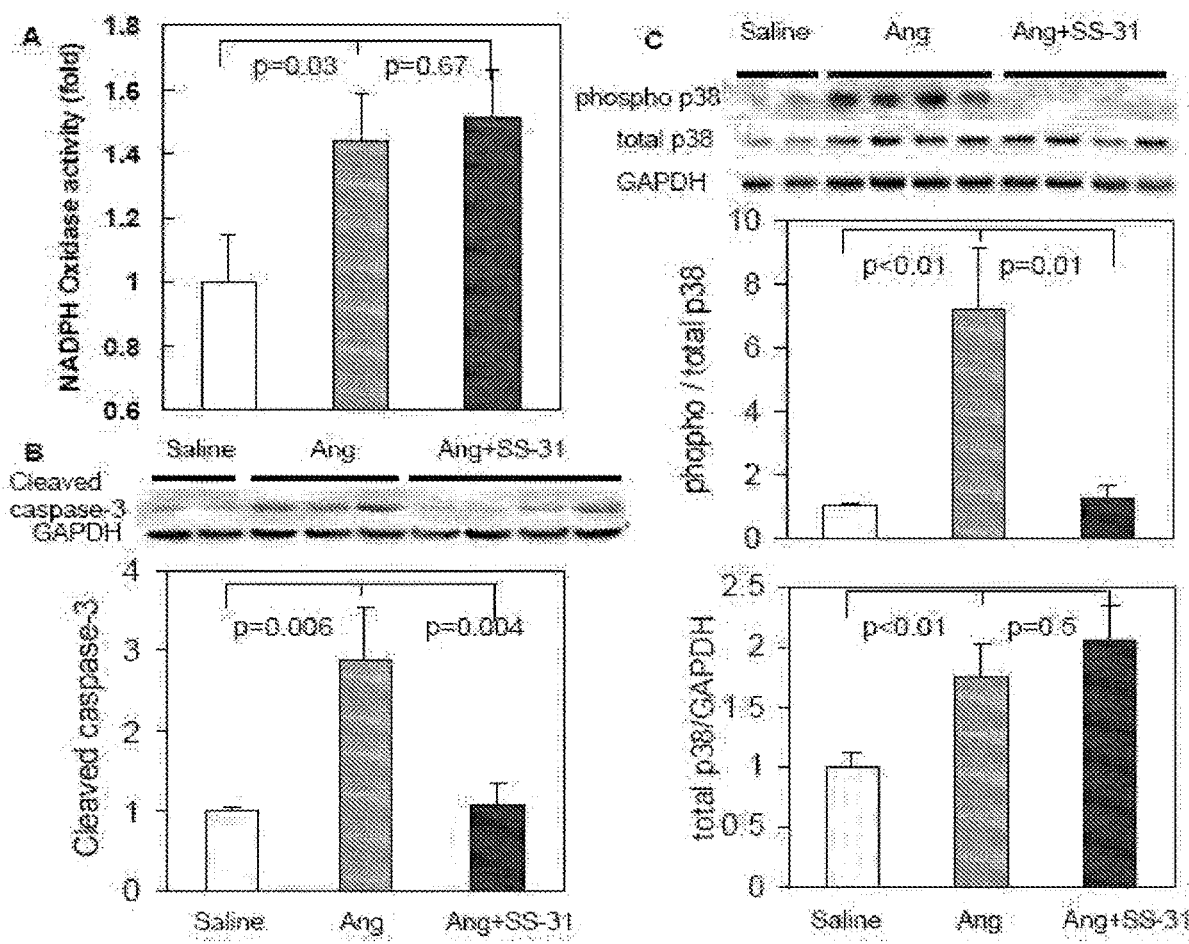
FIGS. 6A-6C are a series of charts showing SS-31 acts downstream of NADPH oxidase and reduces activation of p38 MAPK and apoptosis in response to Ang II.

SS-31 acts downstream of NADPH oxidase and reduces activation of p38 MAPK and apoptosis in response to Ang II. Consistent with previous reports, 4 weeks of Ang II significantly increased cardiac NADPH oxidase activity (p=0.03, FIG. 6A), however, this was not changed by SS-31 administration (p=0.67, FIG. 6A), suggesting that SS-31 protection acts downstream of NADPH oxidase.

Ang II has been shown to activate several mitogen activated protein kinase (MAPK), such as p38. It was confirmed that Ang for 4 weeks increased phosphorylation of p38 MAPK, and this phosphorylation was significantly and nearly fully attenuated by SS-31 (FIG. 6C), suggesting that this MAP kinase is activated through mt-ROS sensitive mechanisms. Mitochondrial ROS, either directly, or indirectly by activating apoptosis signal-regulating kinase, may induce apoptosis. It was found that Ang II did indeed induce cardiac apoptosis, as shown by an approximately 3-fold increase in cleaved (activated) caspase-3 in left ventricular tissue (p=0.006, FIG. 6B). SS-31 completely prevented the activation of caspase-3 caused by Ang II (p=0.004, FIG. 6B).

Figures 9A, 9B, 9C:
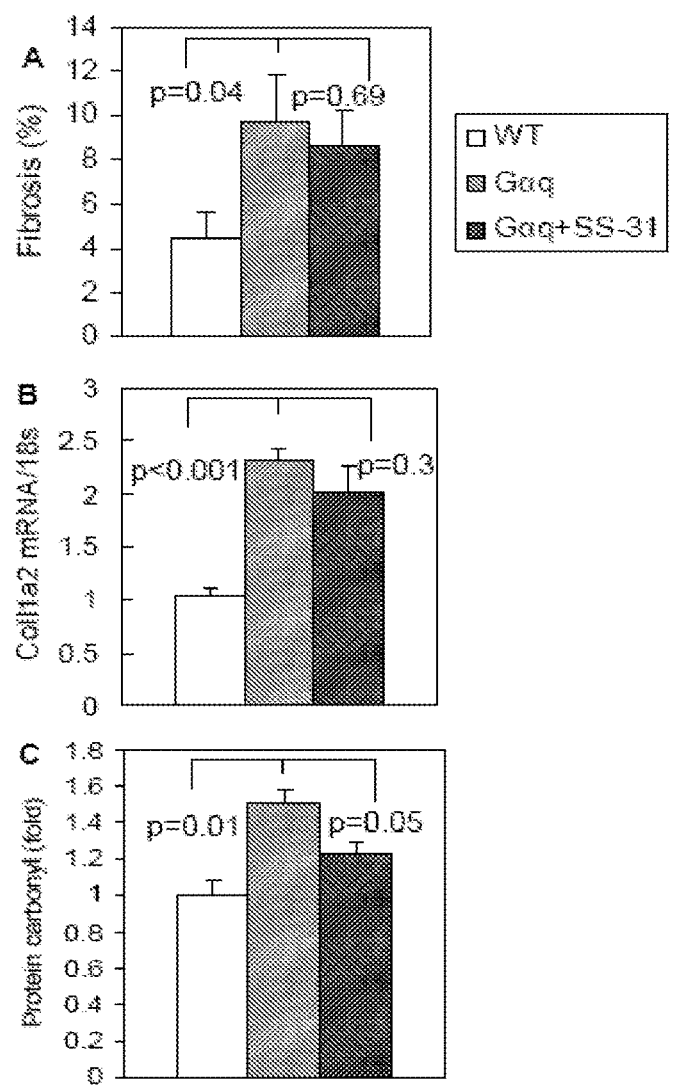
FIGS. 9A-9C are a series of charts showing both cardiac fibrosis and cardiac expression of Coll1a2 gene were not significantly altered by 4 weeks of SS-31 treatment (FIG. 9A and FIG. 9B).

SS-31 partially rescued Gαq overexpression-induced heart failure. Gαq protein is coupled to receptors for catecholamines and Ang II, all of which are known to be key mediators in hypertensive cardiovascular diseases. To extend these observations to a model of chronic catecholamine/Ang II stimulation, a genetic mouse model with cardiac specific overexpression of Gαq was used, which causes heart failure in mice by 14-16 weeks of age. The Gαq mice in this study had impairment of systolic function at 16 weeks age, as shown by a substantial decline in FS (FIG. 7A), with enlargement of the LV chamber (FIG. 7B), impairment of diastolic function indicated by decreased Ea/Aa (FIG. 7C) and worsening of myocardial performance index (MPI, FIG. 7D). SS-31 administered from 12 to 16 weeks of age (3 mg/kg/d) significantly ameliorated systolic function (p<0.001 vs. untreated Gαq, FIG. 7A) and improved myocardial performance (p=0.04, FIG. 7D). LV chamber enlargement was slightly reduced (p=0.08, FIG. 7B), and Ea/Aa was better preserved by SS-31 with borderline significance (p=0.06, FIG. 7C). At 16 weeks of age, normalized heart weights of Gαq mice increased by 33%, while SS-31 substantially reduced cardiac enlargement (p=0.001, FIG. 7E). Lung weights significantly increased by 22% in Gαq mice, indicating lung congestion, and this was slightly attenuated by SS-31 with borderline significance (p=0.09, FIG. 7E). Ventricular fibrosis increased by approximately 2 fold in Gαq mice, which was not changed in SS-31 treated mice (FIG. 9A), and this was confirmed by procollagen 1a2 quantitative PCR (FIG. 9B). Mitochondrial protein oxidative damage is also evident in Gαq hearts (p=0.01, FIG. 9C), and SS-31 treated mice displayed significant reduction of cardiac mitochondrial protein carbonyls (p=0.05, FIG. 9C). There was no evidence of increased cleaved-caspase 3 in Gαq mouse hearts (data not shown).

DISCUSSION

Figure 8:
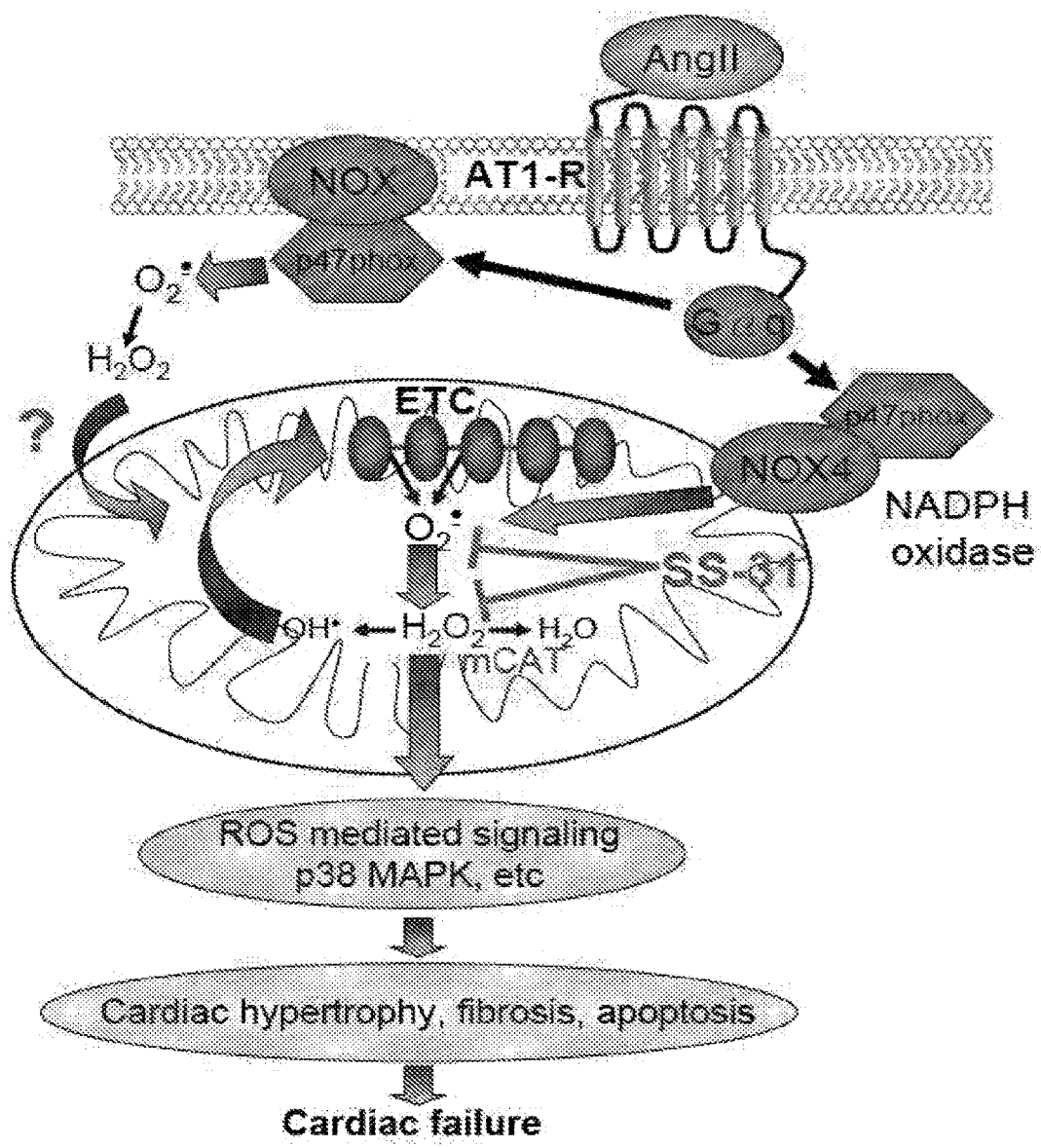
FIG. 8 is a diagrammatic illustration of the proposed effect of mitochondrial antioxidant SS-31 on Ang II and Gαq-induced cardiomyopathy. Mitochondrial antioxidant SS-31 acts downstream to Angiotensin II receptor, Gαq, NADPH oxidase and upstream of p38 MAPK and apoptosis.

The current study demonstrated that exposure to Ang II for 4 weeks increased cardiac mitochondrial protein oxidative damage and induced the signaling for mitochondrial biogenesis (FIG. 5), consistent with the previous report that $H_2O_2$ directly activates transcription of PGC-1α, the master regulator of mitochondrial biogenesis. SS-31 significantly attenuated Ang-induced mitochondrial oxidative stress and hence reduced upregulation of mitochondrial biogenesis, as well as reduced ROS mediated signaling, such as phosphorylation of p38 MAPK (FIG. 8). Furthermore, mitochondrial oxidative stress can lead to apoptosis as a result of cytochrome c release and activation of procaspase-9, followed by caspase-3 activation and apoptosis. These results confirm that attenuation of mitochondrial ROS with SS-31 prevented apoptosis as measured by activated caspase-3 (FIG. 6), concomitant with amelioration of Ang II induced cardiac hypertrophy, fibrosis and diastolic dysfunction (FIGS. 3 and 4).

Figures 7A, 7B, 7C, 7D, 7E:
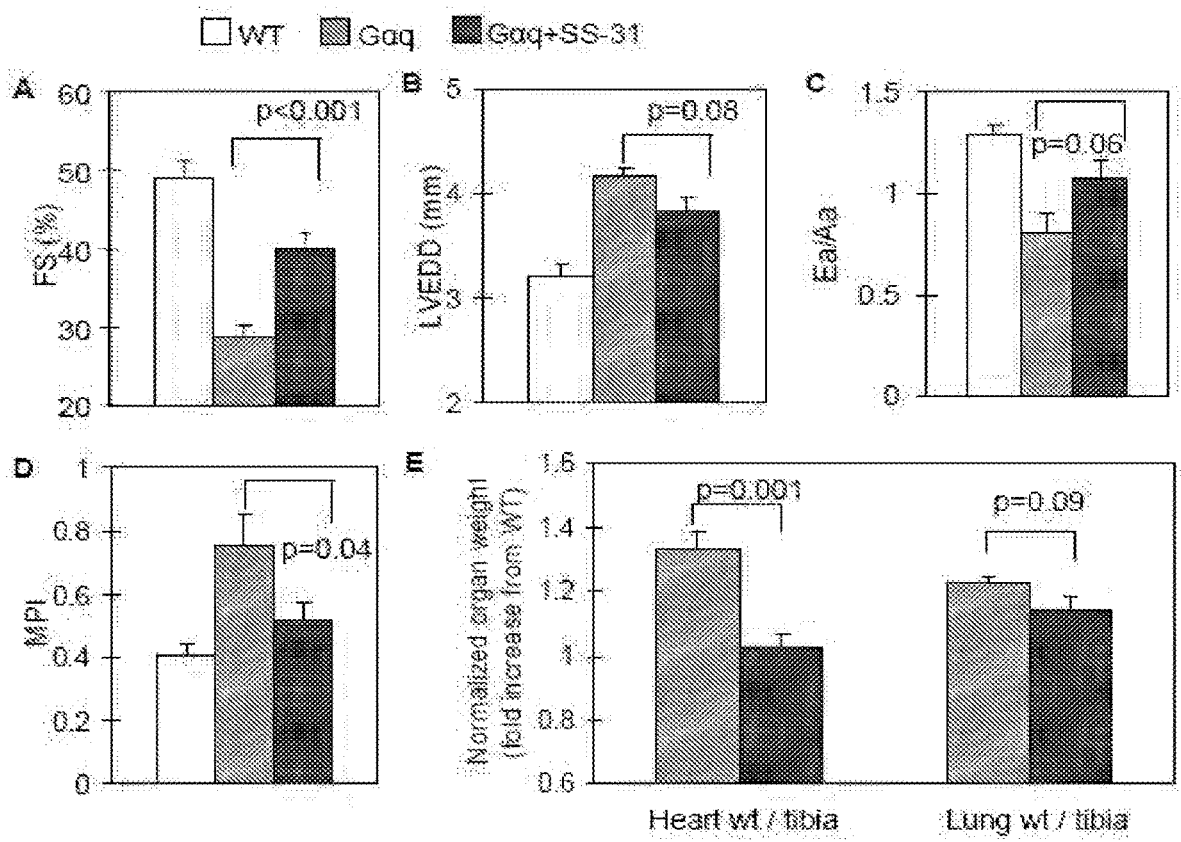
FIGS. 7A-7E are a series of charts showing SS-31 ameliorated cardiac hypertrophy and failure in Gαq overexpressing mice. Echocardiography of Gαq mice with or without SS-31 treatment and WT littermates at 16 weeks of age.

To recapitulate the effect of prolonged neurohormonal stimulation as seen in chronic hypertension on the heart, transgenic mice overexpressing the Gαq protein were used. Gαq is a subunit of the G-protein that is coupled to adrenergic and angiotensin 11 receptors. Cardiac-specific overexpression of Gαq has been shown to cause heart failure in mice by 14-16 weeks of age, despite the absence of increased blood pressure. Twelve-week-old Gαq mice were treated with SS-31 for 4 weeks and demonstrated that SS-31 partially rescued the heart failure phenotype in the Gαq mouse model. SS-31 significantly ameliorated systolic dysfunction, cardiac hypertrophy, and improved overall myocardial performance (FIG. 7A, D, E). A trend showing that SS-31 attenuated chamber enlargement, diastolic dysfunction and lung congestion was also observed (FIGS. 7B, C and E).

Hypertension is a highly prevalent disease that imposes a major risk for the development of atherosclerosis, cardiomyopathy, stroke, sudden cardiac death and heart failure. Hypertension-induced heart failure may be manifested as systolic heart failure or heart failure with preserved ejection fraction (HFpEF); the latter accounts for nearly half of the patients with heart failure, especially among female elderly patients, and the prognosis of HFpEF is marginally better than that of systolic heart failure. Several clinical trials have shown that the current recommended antihypertensive medications are effective in reducing major cardiovascular events and the development of heart failure by only up to 50%. Although this treatment reduces mortality and improves quality of life in patients with established systolic heart failure, there is no convincing evidence for any effective treatment of HFpEF. This underscores the urgent need to develop new prevention and treatment strategies for hypertensive cardiovascular diseases.

In summary, these results indicate that the mitochondrial targeted antioxidant SS-31 is beneficial in amelioration of cardiomyopathy resulting from prolonged Ang II stimulation as well as Gαq overexpression, suggesting its potential clinical application for target organ protection in hypertensive cardiovascular diseases. As such, the aromatic-cationic peptides of the invention are useful in methods for treating or preventing HF in mammalian subjects.

Example 2—Treatment or Prevention of Heart Failure in an Animal Model Using SS-20
(Prophetic)

The effects of the aromatic-cationic peptide SS-20 in treating or preventing heart failure are examined in an Ang II mouse model or a Gαq mouse model.

The study is carried out in C57Bl6 mice. Ang II is infused by osmotic minipump (4 weeks @ 1.1 mg/kg/d) to the mice in the following groups: (1) wild type (WT); (2) transgenic mice exhibiting cardiac specific overexpression of angiotensinogen (Tg); (3) mice overexpressing catalase targeted to peroxisomes (pCAT); mice overexpressing catalase targeting to mitochondria (mCAT); and (4) mice expressing an inducible mCAT (i-mCAT). In mice that receive SS-20, the SS-20 is put into the same minipump with Ang II and infused at a rate of 3 mg/kg/d for 4 weeks.

Alternatively, the study is carried out in C57Bl6 mice in the following treatment groups: (1) WT (wild-type C57Bl6 mice); (2) pCAT (overexpression of catalase targeted to peroxisomes); (3) mCAT (overexpression of catalase targeted to mitochondria); (4) Gαq (overexpression of Gαaq); (5) Gαq/mCAT (overexpression of Gαq and mitochondria-targeted catalase); (6) Gαq/pCAT (overexpression of Gαq and peroxisome-targeted catalase); and (7) Gαq+SS-peptides (Gαq mice treated with SS-20).

Cardiac function is determined by echocardiography (Acuson CV-70, Siemens Medical Systems, Malvern, PA) using standard imaging planes—M-mode, conventional, and tissue Doppler imaging. The myocardial performance index (MPI), left ventricular mass index (LVMI), and Ea/Aa ratio are measured as described in Example 1.

Treatment with SS-20 is predicted to reduce Ang II-induced HF or Gαq-induced HF as evidenced by a reduction in LVMI and MPT, and no increase in heart weight. There is also predicted to be an improvement in both systolic and diastolic function. The protection provided by SS-20 is expected to be similar to the protection provided by overexpression of catalase in mitochondria. As such, aromatic-cationic peptide SS-20 is useful in methods at preventing or treating hypertensive cardiomyopathy and HF in mammalian subjects.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method of treating hypertensive cardiomyopathy in a mammalian subject, comprising administering to the mammalian subject in need thereof a therapeutically effective amount of the peptide D-Arg-2'6'-Dmt-Lys-Phe-NH$_2$.

2. The method of claim 1, wherein the subject is suffering from heart failure.

3. The method of claim 1, wherein myocardial contractility and cardiac output in the subject administered the peptide are increased compared to a control subject not administered the peptide.

4. The method of claim 3, wherein the myocardial contractility and cardiac output in the subject are increased at least 10% compared to a control subject not administered the peptide.

5. The method of claim 1, wherein the subject is a human.

6. The method of claim 1, wherein the peptide is administered orally, topically, systemically, intravenously, subcutaneously, intraperitoneally, or intramuscularly.

7. The method of claim 1, further comprising separately, sequentially or simultaneously administering a cardiovascular agent to the subject.

8. The method of claim 7, wherein the cardiovascular agent is selected from the group consisting of: an anti-arrhthymia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, a *digitalis* formulation, an inotrope, and an antihyperlipidemic drug.

9. A method for increasing myocardial contractility and cardiac output in a subject suffering from hypertensive cardiomyopathy comprising administering to the subject a therapeutically effective amount of the peptide D-Arg-2'6'-Dmt-Lys-Phe-NH$_2$.

* * * * *